United States Patent
Wong et al.

(10) Patent No.: US 7,238,943 B2
(45) Date of Patent: Jul. 3, 2007

(54) ASYMMETRICALLY PLACED CROSS-COUPLED SCINTILLATION CRYSTALS

(75) Inventors: Wai-Hoi Wong, Houston, TX (US); Jorge Uribe, Houston, TX (US); Hossain Baghaei, Sugarland, TX (US); Hongdi Li, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/356,679

(22) Filed: Jan. 31, 2003

(65) Prior Publication Data

US 2004/0021082 A1 Feb. 5, 2004

Related U.S. Application Data

(60) Provisional application No. 60/353,135, filed on Feb. 1, 2002.

(51) Int. Cl.
*G01T 1/164* (2006.01)
*G01T 1/202* (2006.01)

(52) U.S. Cl. ............ 250/367; 250/363.03; 250/363.04; 250/370.11

(58) Field of Classification Search ................ 250/367, 250/370.11, 362, 363.03, 366
See application file for complete search history.

(56) References Cited

U.S. PATENT DOCUMENTS

| 3,225,193 | A | * | 12/1965 | Hilton et al. | 250/367 |
| 3,621,256 | A | * | 11/1971 | Cacheux et al. | 250/370.01 |
| 4,037,105 | A | | 7/1977 | Laurer | 250/367 |
| 4,153,839 | A | * | 5/1979 | Hounsfield et al. | 250/370.09 |
| 4,234,792 | A | * | 11/1980 | DeCou et al. | 250/370.09 |
| 4,291,228 | A | * | 9/1981 | Thompson | 250/363.03 |
| 4,338,521 | A | | 7/1982 | Shaw et al. | 250/370.11 |
| 4,656,359 | A | | 4/1987 | Persyk et al. | 250/486.1 |

(Continued)

FOREIGN PATENT DOCUMENTS

JP   08233942 A  *  9/1996

(Continued)

OTHER PUBLICATIONS

Wong et al., "An elongated position sensitive block detector design using the PMT quadrant sharing configuration and asymmetric light partition," 1998 Nuclear Science Symposium, vol. 2, pp. 1204-1207, Nov. 1998.*

(Continued)

*Primary Examiner*—David Porta
*Assistant Examiner*—Frederick F. Rosenberger
(74) *Attorney, Agent, or Firm*—Fulbright & Jaworski LLP

(57) ABSTRACT

Systems and methods are described for asymmetrically placed cross-coupled scintillation crystals. A method includes coupling a plurality of photomultiplier tubes to a scintillation crystal array, the scintillation crystal array defining a plurality of corner edges, wherein a first corner edge of the plurality of corner edges is aligned with a first center of a first photomultiplier tube of the plurality of photomultiplier tubes and a second corner edge of the plurality of corner edges is not aligned with a second center of a second photomultiplier tube of the plurality of photomultiplier tubes.

29 Claims, 25 Drawing Sheets
(3 of 25 Drawing Sheet(s) Filed in Color)

U.S. PATENT DOCUMENTS

| | | | | |
|---|---|---|---|---|
| 4,733,083 | A | | 3/1988 | Wong .......................... 250/363 |
| 4,743,764 | A | * | 5/1988 | Casey et al. ............ 250/363.03 |
| 4,750,972 | A | | 6/1988 | Casey et al. ................... 216/24 |
| 4,864,138 | A | * | 9/1989 | Mullani .................. 250/363.03 |
| 4,883,966 | A | | 11/1989 | Wong ..................... 250/363.02 |
| 5,010,251 | A | | 4/1991 | Grinberg et al. .............. 250/332 |
| 5,032,728 | A | * | 7/1991 | Chang et al. ............ 250/363.04 |
| 5,091,650 | A | | 2/1992 | Uchida et al. ............... 250/366 |
| 5,149,956 | A | | 9/1992 | Norton ........................ 257/188 |
| 5,241,180 | A | * | 8/1993 | Ishaque et al. .......... 250/361 R |
| 5,258,145 | A | | 11/1993 | Nelson ......................... 264/21 |
| 5,319,204 | A | | 6/1994 | Wong ..................... 250/363.03 |
| 5,453,623 | A | | 9/1995 | Wong et al. ............ 250/363.03 |
| 5,786,597 | A | | 7/1998 | Lingren et al. ......... 250/370.09 |
| 6,087,663 | A | | 7/2000 | Moisan et al. ............... 250/367 |
| 6,091,796 | A | | 7/2000 | Trissel et al. .................. 378/43 |
| 6,288,399 | B1 | * | 9/2001 | Andreaco et al. ............ 250/368 |

FOREIGN PATENT DOCUMENTS

WO     WO 00/21142     4/2000

OTHER PUBLICATIONS

Drobyshev et al., "Optimization of the lead-tungstate crystal/photodetector system for high energy physics," 1994 Nuclear Science Symposium and Medical Imaging Conference, vol. 1, pp. 14-17, Nov. 1994.*

Aykac et al., "Septa Design Study for Volumetric Imaging in Positron Emission Tomography", IEEE MIC Conference Record, 2001.

Chang et al., "A multi-detector cylindrical spect system for phantom imaging," IEEE, 90CH2975:1208-1211, 1990.

Digby et al., "Detector, shielding and geometric design factors for a high resolution PET system," IEEE Trans. on Nucl. Sci., 37(2):664-670, 1990.

Huesman et al., "List-mode maximum-likelihood reconstruction applied to positron emission mammography (PEM) with irregular sampling," IEEE Trans. Med. Imaging, 19(5):532-537, 2000.

Li et al., "A high speed position-decoding electronics for BGO block detectors in PET," IEEE Trans. Nucl. Sci., 47(3):1006-1010, 2000.

Li et al., "A new pileup prevention front-end electronic design for high resolution PET and gamma cameras," IEEE MIC Conference Record, 2001.

Muehllehner et al., "A hexagonal bar positron camera: problems and solutions," IEEE Trans. on Nucl. Sci., NS-30(1): 652-660, 1983.

Tornai et al., "Position and energy response of PET block detectors with different light sharing schemes," IEEE Trans. Nucl. Sci., 41(4):1458-1463, 1994.

Uribe et al., "Basic imaging performance characteristics of a variable field of view PET using quadrant sharing detectors," IEEE Trans. Nucl. Sci., 46(6):491-497, 1999.

Uribe et al., "Inexpensive Positon Sensitive Detector Block for 40 mm Diameter PMT Using Quadrant Sharing Configuration," IEEE Medical Imaging Conference, Nov. 10, 2001.

Weitzman and Lituchy, "PET scan," from the HeartCenterOnline for patients website. www.heartcenteronline.com/myheartdr/common/articles.cfm?ARTID=451, 2000.

Wong et al., "A slanting light-guide analog decoding high resolution detector for positron emission tomography camera," IEEE Trans. on Nuclear Sci., NS-34:280-284, 1987.

Wong et al., "An elongated position sensitive block detector design using the PMT quadrant sharing detector array," IEEE Trans. Nucl. Sci., 46(3):542-545, 1999.

Wong et al., "Characteristics of small barium fluoride ($BaF_2$) scintillator for high intrinsic resolution of time-of-flight position emission tomography," IEEE Trans. on Nuclear Sci., NS-31:381-386, 1984.

Wong et al., "Feasibility of a high speed gamma camera using the high-yield-pileup-event-recovery (HYPER) method," J. Nucl. Med., 42(4):624-632, 2001.

Wong et al., "The design of a high resolution transformable wholebody PET camera," IEEE Transactions on Nuclear Science, 49:2079-2084, 2002.

Wong, "A positron camera detector design with corss coupled scintillators and quadrant sharing photomultipliers," IEEE Trans. Nucl. Sci., 40:962-966, 1993.

Yamamoto et al., "A BGO detector unit for a stationary high resolution positron emission tomograph," J. of Comptuer Assisted Tomography, 10(5):851-855.

Zhang et al., "performance stability of SHR-2000 high resolution PET for animal research," Ann. Nucl. Med., 13(1):65-70, 1999.

Ziegler et al., "A prototype high-resolution animal positron tomograph with avalanche photodiode arrays and LSO crystals," Eur. J. Nucl. Med., 28(2):136-143, 2001.

* cited by examiner

910

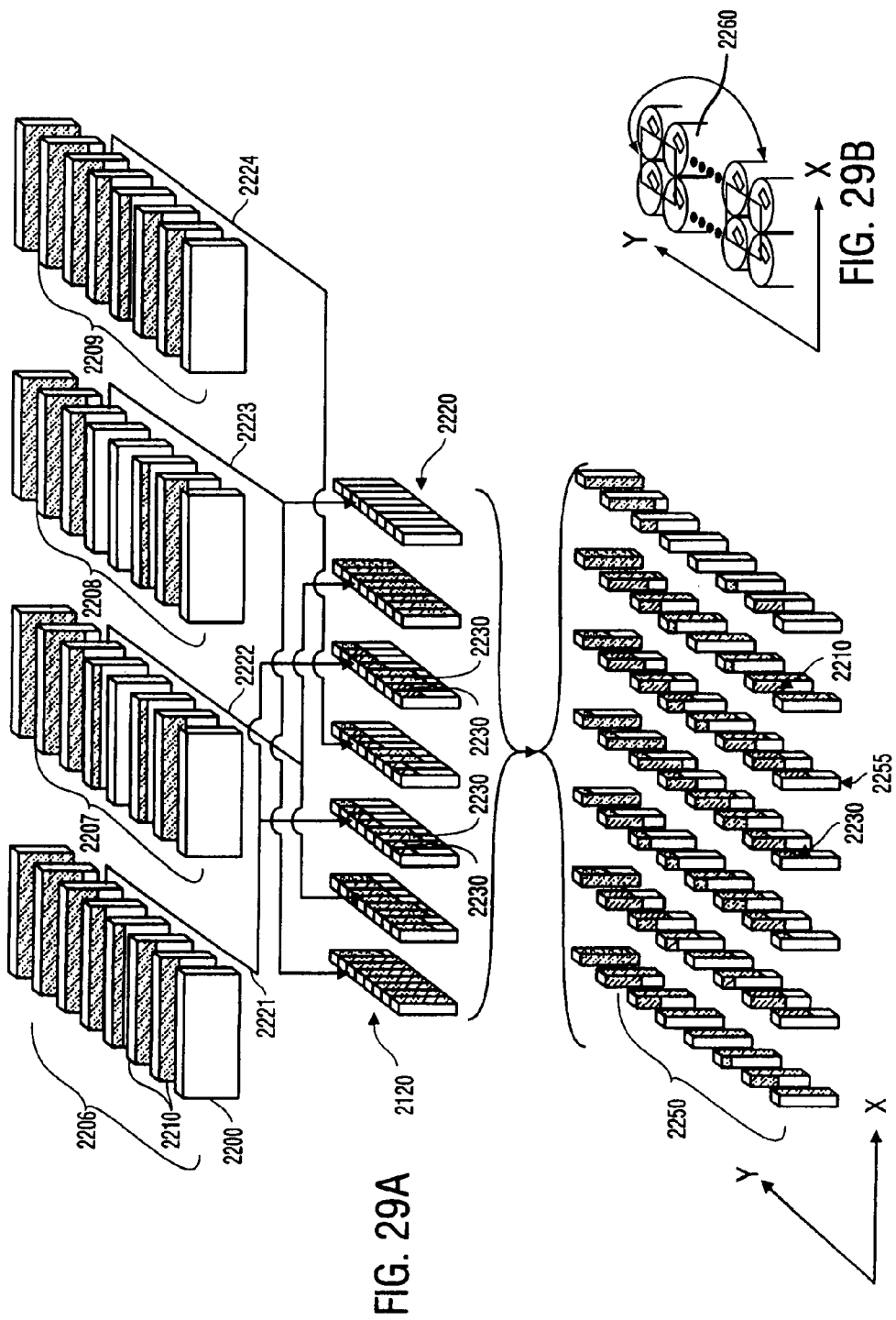

ASYMMETRICALLY PLACED CROSS-COUPLED SCINTILLATION CRYSTALS

CROSS-REFERENCE TO RELATED APPLICATION

This application is related to and claims a benefit of priority to U.S. Ser. No. 60/353,135, filed on Feb. 1, 2002, the entire contents of which are hereby expressly incorporated by reference for all purposes.

STATEMENT AS TO RIGHTS TO INVENTIONS MADE UNDER FEDERALLY-SPONSORED RESEARCH AND DEVELOPMENT

This invention was made with United States Government support under contract to the National Institute of Health. The Government may have certain rights in this invention.

BACKGROUND OF THE INVENTION

1. Field of the Invention

The invention relates generally to the field of Positron Emission Tomography (PET). More particularly, the invention relates to scintillation radiation detectors in PETs. Specifically, a preferred implementation of the invention relates to the manufacture of the scintillation radiation detectors.

2. Discussion of the Related Art

Positron emission tomography (PET) is a technique for measuring the concentrations of positron emitting radioisotopes within the tissue of living subjects and using those measurements to form images of the internal tissues. PET may require a cyclotron as an on-site source of short-lived positron-emitting isotopes. The isotopes are injected into the patient along with a glucose-related compound, and the positrons collide with electrons in body tissues to produce photons. The photons are tracked by a tomographic scintillation detector, and the information is processed by a computer to provide both images and data on blood flow and metabolic processes within the tissues observed.

The tomographic scintillation detector is a vital part of the PET. Without it, imaging of the tissues cannot take place. The detectors are arranged into arrays. Each array is a matrix of scintillation crystals, each optionally rectangular in shape. When a gamma or other radiation particle strikes a crystal detector element in the array, light is emitted. The light signal is distributed to four or more photosensors, as shown in FIGS. 1–3. The amount of light going to each of the photosensors from this stimulated detector, a transparent crystal, is controlled by either some light partition or coupling between the crystals, or by a light guide system between the crystal array and the photosensors. The four or more photosensors turn the light signals into proportional electronic signals. The relative magnitude of the electronic signals from the four or more photosensors is used to deduce the position of the scintillating crystal. This type of position-sensitive detection system is widely used in radiation imaging. The performance of the system is determined by the accuracy of deducing the position of the scintillating crystal. The accuracy of decoding the position is in turn determined by the design of the light-partition, light coupling or light-guide.

As shown in FIG. 2, one traditional way of building a detector array with the optimal light distribution is as follows: a solid crystal block that is cut with unequal saw-cut depth in both the transaxial and axial dimensions. This process is satisfactory for the larger crystal elements used in lower resolution cameras but not for the very high resolution, small crystal elements, cameras. One reason is the substantial loss in coincidence detection efficiency for very small detectors due to the width of the grooves created by the saw blade, as PET coincidence detection efficiency=(detector efficiency)$^2$=(detector transaxial packing fraction×axial packing fraction)×(detector transaxial packing fraction×axial packing fraction).

If the detector pitch is 1.7 mm, which couples to a saw-blade groove of 0.4 mm (typical), the detector packing fraction would be (1.7−0.4)/1.7=0.76 along both the transaxial and axial dimension. Hence, for the case of a PET camera, the coincidence efficiency can be (0.76×0.76)$^2$=0.33. In other words, 67% of the coincidence events will be lost by the saw cut for a detector pitch of 1.7×1.7 mm.

As shown in FIG. 3, a second way of making position-sensitive detectors is to put individual crystals, each optically isolated by painting or masking all the 4 side surfaces, onto a light-guide plastic block that has unequal grooves cut into it. In this case, the unequal grooves are in the light guide instead of the crystal block. The crystals need to be individually cut and polished. Then the individual crystals are placed and glued onto the light guide manually or by a robotics device. In either case, there is a gap between crystals for the clearance of the tweezers or robotics fingers that grab and place the crystals onto the light guide. However, the gaps between the crystals also reduce detection sensitivities. Furthermore, since individual crystals have to be cut and polished mechanically or chemically, this process is more labor intensive.

A problem with manufacturing individual crystals for the detectors is in the actual placement of the individual crystals into the array. Mechanical precision is important in the manufacturing of imaging detector systems because tens of thousands of scintillation crystals are closely packed together. These crystals are often very small: 1–5 mm. The buildup of tens of thousands of small mechanical errors (i.e., 0.1 mm per detector) can be a significant error relative to the small sizes of the crystals, which can place some crystals in the detector arrays too far from its expected position, which can degrade the imaging accuracy. What is needed is a method of manufacturing that can decrease the total sum of mechanical errors caused during the making of the detector arrays.

Another disadvantage of conventional approaches has been the high cost of manufacturing each crystal individually. Therefore, what is also needed is a solution that meets the above-discussed requirements in a more cost-effective manner.

Yet another way of creating detector arrays is to cut out channels in the scintillation block material and then covering the channels and grooves with a light reflecting material. This is an improvement over the previous methods because it allows the interval between respective channels in a detector array and enhances the arrangement accuracy of the respective channels.

A problem with cutting uneven grooves into the scintillation material has been that the depth of the cut in the crystal is very deep at the ends of the block, and the small amount of material left to connect the channels is easily breakable. If the material breaks, the whole detector crystal block is wasted and unusable. Therefore, what is required is a solution that is less prone to breakage and that will not render the whole detector useless when a portion of it fails or breaks off.

For the manufacture of circular detector arrays, additional grinding of the scintillation crystals is needed to eliminate the crystal overlap present in a circular detector arrangement. This additional process may be time and cost extensive, as it may require the grinding of each individual crystal. For scintillation crystals blocks created by cutting groves into the blocks, additional grinding may increase the odds of creating a defective crystal block by breaking off crystals at the ends of the blocks.

Heretofore, the requirements of a more durable scintillation detector array, decreased mechanical errors in the arrays, decreased gaps between crystals, and decreased cost of capital and time in the manufacturing of the detector arrays have not been fully met. What is needed is a solution that addresses some or all of these requirements.

SUMMARY OF THE INVENTION

There is a need for the following embodiments. Of course, the invention is not limited to these embodiments.

According to one aspect of the invention, a method comprises coupling a plurality of photomultiplier tubes to a scintillation crystal array, the scintillation crystal array defining a plurality of corner edges, wherein a first corner edge of the plurality of corner edges is aligned with a first center of a first photomultiplier tube of the plurality of photomultiplier tubes and a second corner edge of the plurality of corner edges is not aligned with a second center of a second photomultiplier tube of the plurality of photomultiplier tubes.

According to another aspect of the invention, a method comprises detecting radiation with a scintillation crystal array coupled to a plurality of photomultiplier tubes, the scintillation crystal array defining a plurality of corner edges, wherein a first corner edge of the plurality of corner edges is aligned with a first center of a first photomultiplier tube of the plurality of photomultiplier tubes and a second corner edge of the plurality of corner edges is not aligned with a second center of a second photomultiplier tube of the plurality of photomultiplier tubes.

According to another aspect of the invention, an apparatus comprises: a plurality of photomultiplier tubes; and a scintillation crystal array coupled to the plurality of photomultiplier tubes, the scintillation crystal array defining a plurality of corner edges, wherein a first corner edge of the plurality of corner edges is aligned with a first center of a first photomultiplier tube of the plurality of photomultiplier tubes and a second corner edge of the plurality of corner edges is not aligned with a second center of a second photomultiplier tube of the plurality of photomultiplier tubes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings accompanying and forming part of this specification are included to depict certain aspects of the invention. The invention may be better understood by reference to one or more of these drawings in combination with the description presented herein. It should be noted that the features illustrated in the drawings are not necessarily drawn to scale.

FIG. 29 illustrates another embodiment of the invention.

DESCRIPTION OF PREFERRED EMBODIMENTS

Figure 1:
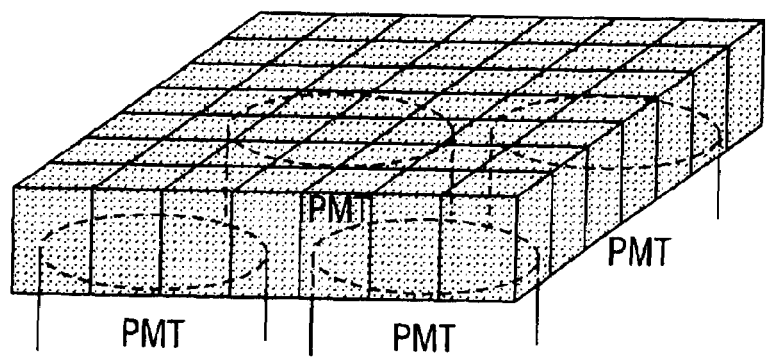
FIG. 1 illustrates a prior-art position-sensitive detector array with 7×7 crystals optically coupled to four photomultiplier photosensors (PMT).
Figure 2A:
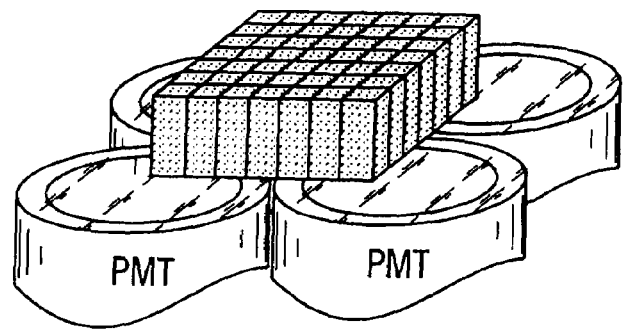
FIG. 2 illustrates prior-art examples of position-sensitive detector array/block with uneven cuts to control light distribution.
Figure 2B:
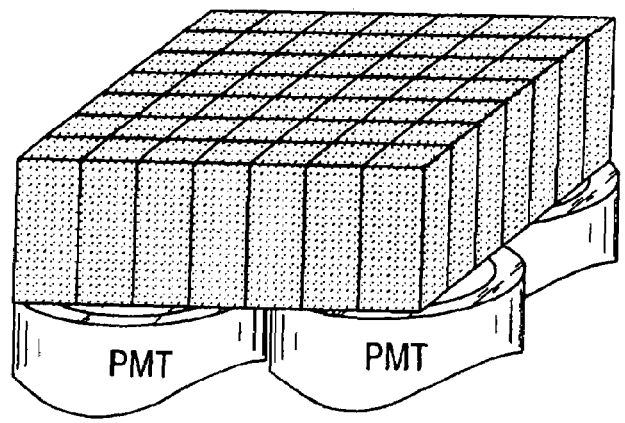
Figure 3A:
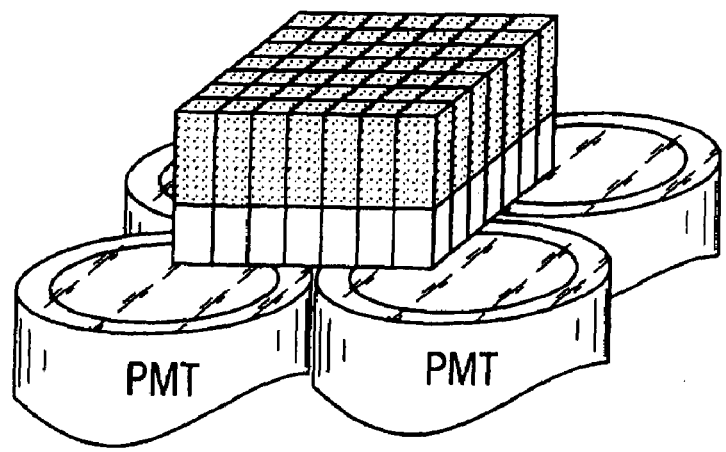
FIG. 3 illustrates prior-art examples of position-sensitive detectors with light guides to control light distribution. The individual crystals are optically isolated and the light guides have uneven cuts.
Figure 3B:
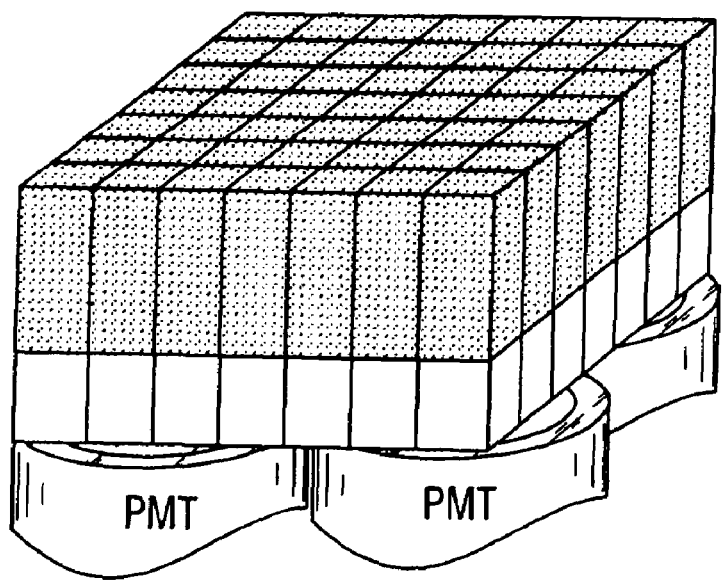
Figure 4:
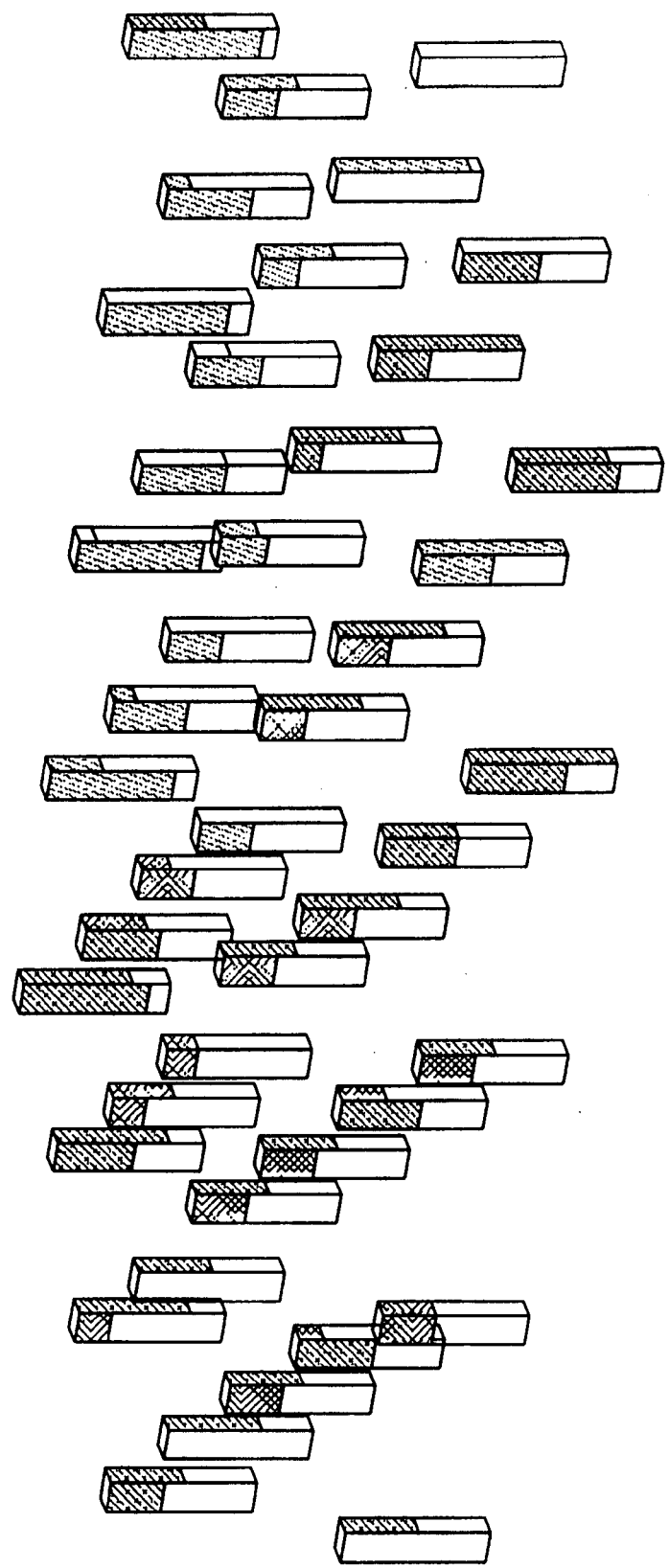
FIG. 4 illustrates a matrix of 8×8 individual scintillation crystals with an optimal light-mask design. This matrix of individual crystals is to be optically glued together to form one finished position-sensitive detector array/block.

The invention can include increased sensitivity of PET detectors. The invention can also include increased efficiency in the manufacturing of PET detectors.

Positron emission tomography (PET) is a technique for measuring the concentrations of positron emitting radioisotopes within the tissue of living subjects and using those measurements to form images of the internal tissues. As such, the detection sensitivity of the detector arrays in the PET apparatus is important.

Detector arrays generally comprise scintillation crystal blocks and PMTs. Conventional methods of manufacturing these crystal blocks include cutting grooves into individual blocks to form smaller crystal elements that are joined together at the crystal block base and cutting individual crystals, also called needles, and placing them individually into detector arrays. The separations remaining between each needle and the grooves cut into the crystal blocks cause distortions in the images resulting from detection of radioisotopes in the subject.

If a painted optical mask between the scintillation detector crystals is used in making the detector arrays, instead of the previously mentioned methods, the detection sensitivity can be increased. A painted optical mask has an approximate thickness of 0.04 mm, for an approximately 1.7× approximately 1.7 mm pitch array, which provides a coincidence efficiency of approximately 0.95. Hence, replacing saw cuts by the proposed painted optical masks increases coincidence detection efficiency by 2.9 times and also improves image quality, which is significant.

Furthermore, since one can paint on any mask pattern, this flexibility over the saw cut method allows finer tuning of the light distribution to the photosensors which translates to better position decoding accuracy to achieve better image resolution. However, the proposed painted mask technique can be extremely labor intensive if it is applied to each crystal individually, which may render it impractical. With approximately 38,000 individual detector elements in a high resolution PET (referring to FIG. 26, the detector module depicted has 4 8×8 arrays (256 crystals), 24 7×8 arrays (1344 crystals), and 32 7×7 crystals (1568); in a PET camera with 12 modules, there are [(256+1344+1568)×12]=38016 crystals), and with four painted masks on each element, there will be approximately 152,000 (e.g. 152,064) surfaces for painting. These surfaces will also need to be organized and glued together to form the arrays. This would be a highly tedious undertaking, not to mention the cost of buying the individual crystals, also known as needles.

The invention bypasses this problem by utilizing a slab-sandwich-slice (SSS) method of production. This technique potentially lowers the processing cost, increases yield by causing less breakage, and increases the detection efficiency.

Slab-Sandwich-Slice Method

Each crystal array in a detector is a matrix of scintillation crystals (transparent crystals), each optionally rectangular in shape. When a gamma or other radiation particle strikes a detector element (crystal) in the array, light is emitted.

The light signal is distributed to 4 or more photosensors. The amount of light going to each of the photosensors from this stimulated detector is controlled by (a) some light partition or coupling between the crystals, or (b) by a light-guide system between the crystal array and the adjacent photosensors.

The 4 or more photosensors are used to deduce the position of the scintillating crystal. This type of position-sensitive detection system is widely used in radiation imaging. The performance of the system is determined by the accuracy of deducing the position of the scintillating crystal. The accuracy of decoding the position is in turn determined by the design of the light-partition, light coupling or light guide.

This invention reduces the amount of work involved in creating these detectors. The number of production steps is reduced from $N^2$ to 2N (like the Fourier Transform) where N×N is the crystal matrix size, since slabs and slices are being used in each step, instead of individual crystals in each production step. In fact, the longer the starting slabs are, the more efficient this process becomes.

In this process, individual slabs of length N may be painted with a mask pattern or differing mask patterns. These slabs are glued together using an optical glue to form sandwiches. These sandwiches are then sliced into sandwich slices, the thickness of each sandwich slice being equal to the thickness of one equivalent crystal element. These sandwich slices may be painted with additional mask patterns before being glued together with optical glue to form a detector array. Slices from different sandwiches with different mask patterns may be glued together to obtain a desired light guide pattern in the detector array.

Figure 5:
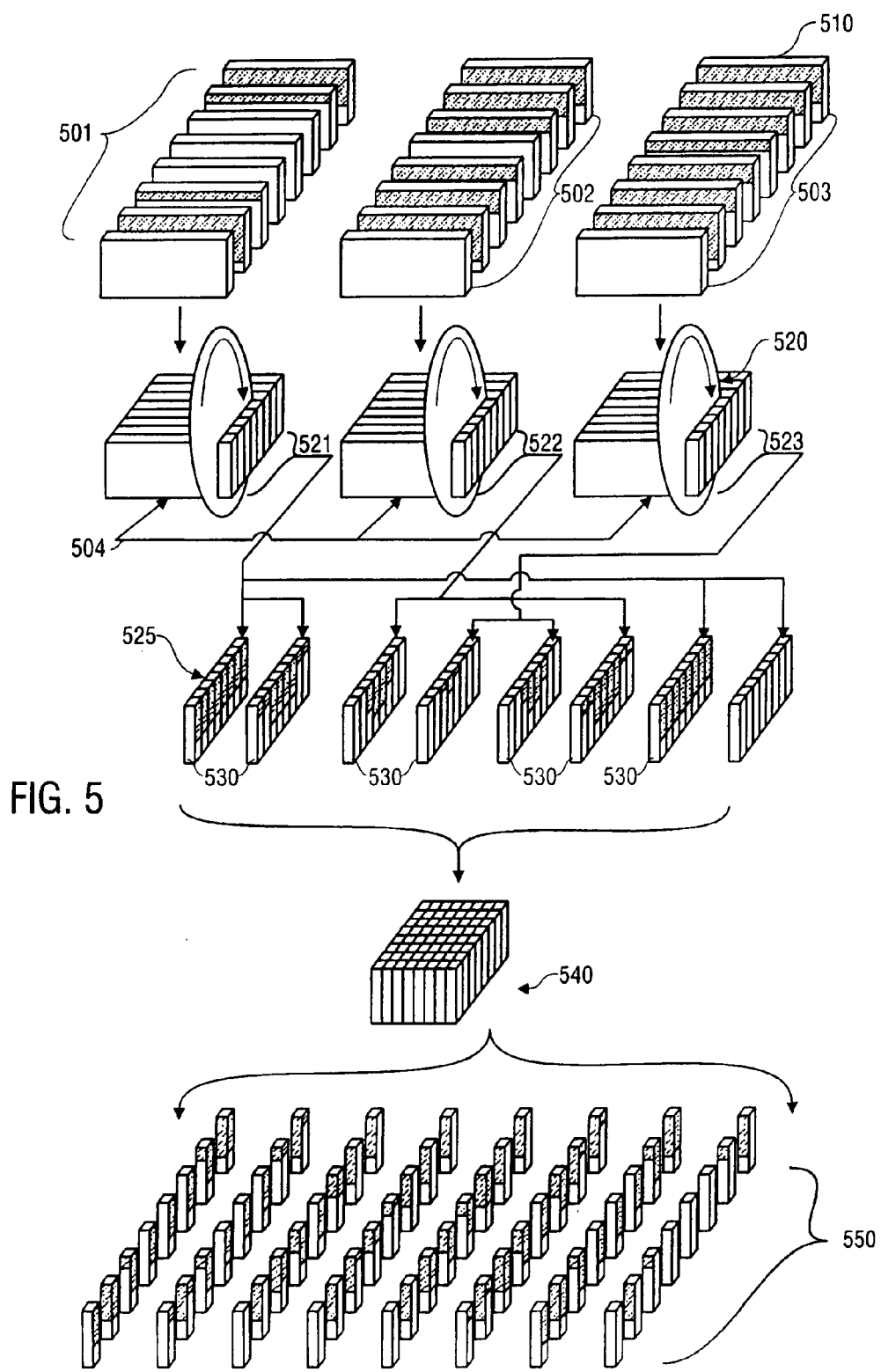
FIG. 5 illustrates the slab-sandwich-slice production method for making position-sensitive detectors.

For example, a slab could be used which has the same dimensions as 25 needles stacked together side by side. This would cost significantly less than the aforementioned method. This exemplary production algorithm is illustrated in FIG. 5. The optical mask design utilizes as many symmetries as possible to minimize production parts and procedures.

All the slabs are assembled into several different sandwich types 501, 502, 503. Each sandwich is a stack of eight slabs painted with optical masks 510 and optically glued together to form an 8×1 detector sandwich. Each type has a different set of interslab painted masks 510, and FIG. 5 illustrates the process for a three-type sandwich construction. In Type A 501, four of the eight slabs are painted with two different mask patterns. For Type B 502, six slabs are painted with three different mask patterns. For Type C 503, seven slabs can be painted with four different mask patterns.

These painted slabs are then optically glued together to form each sandwich type 504. A total of 192 sandwiches are needed to produce 576 arrays, each with 64 crystals, for a hypothetical camera with 36,864 crystals.

The number of sandwich-types needed depends on the size of each detector array. It can range between just having one type to several types depending on the detail detector design. The detector detail design depends on a number of variables including the final crystal-array matrix size, the type of crystals used, the exact geometry of each crystal element, and the type, size, shape and optical characteristics of the photosensors. Examples 1–3 illustrate this method using different masks and sandwich types.

All of these sandwiches 504 are crosscut into slices 520, and each slice is equivalent to every other slice from the same sandwich type. The thickness of each slice is again one crystal width. Four slices 521 cut from the Type A sandwich 501 are used for the first two and last two columns of a detector array. Two slices 522 cut from the Type B sandwich 502 are used for the third and sixth columns of an 8×8 array, and 2 slices 523 from the Type C sandwich 503 can be used for the middle two columns of an array. These eight new slices are painted 525 with seven new masks 530 and then optically glued together to form a finished array. A special gluing jig/holder is used to glue the slices together with high precision in 3 dimensions to form the final array 540. An expanded view 550 of the final array 540 is shown.

Optical Masks and Optical Glue

Figure 7A:
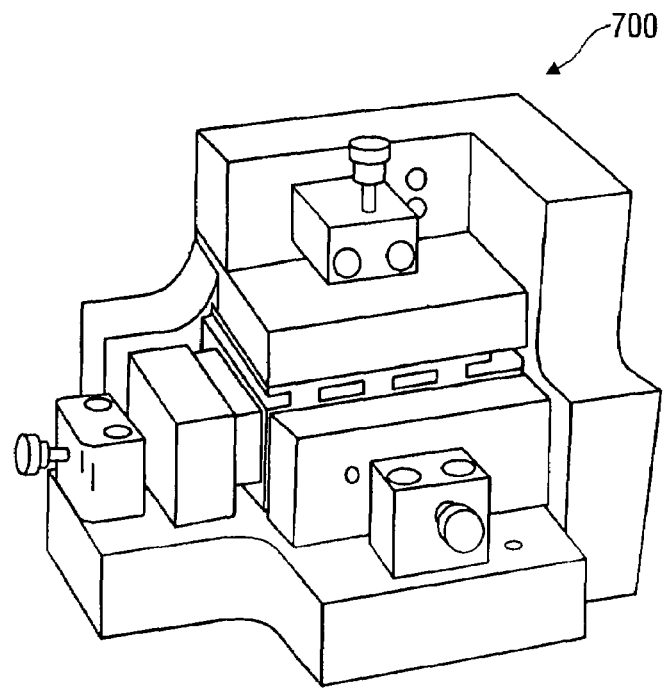
FIGS. 7A–7B illustrate embodiments of a gluing jig.
Figure 7B:
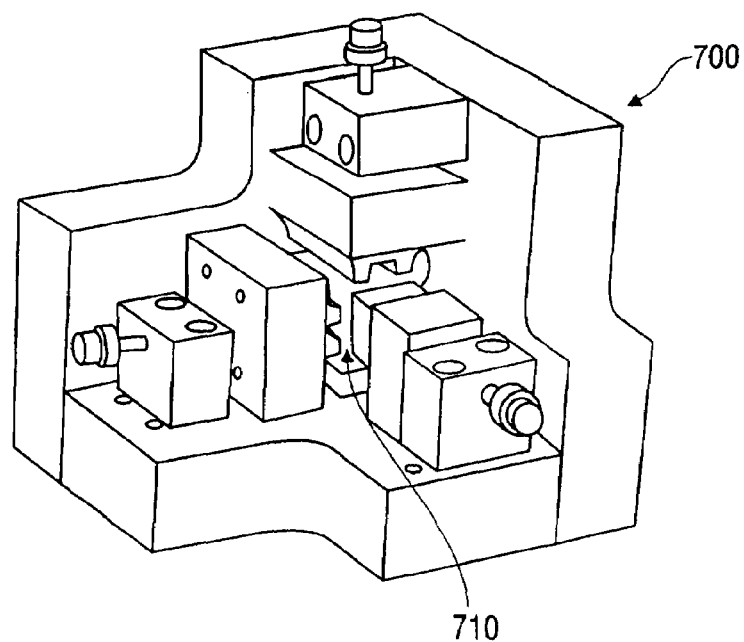

The optical glue is any glue that is optically transparent and bonds permanently once dry. The glue will allow very little absorption or scattering of light. Once the glue has been applied, it is placed into a gluing jig or holder 700, shown in FIG. 7A and FIG. 7B. This apparatus helps to glue the slab-sandwiches and final detector blocks to an exact dimension so that the glue-thickness can be controlled. The cleaning of excess glue from the block can also be simplified. There are draining spaces 710 for the excess glue so that it minimizes the amount of excess glue remaining on the slab-sandwich or detector block.

Optical masks are painted onto slabs of scintillation crystal, instead of individual needles, in a pre-determined pattern. The slabs are then optically glued together, and sliced into columns. The columns are painted with another optical mask pattern. The resulting columns are glued together to form the desired arrays.

The optical mask on the slabs and slices has a high reflection efficiency and bounces light back into the crystal. It can be applied like a paint, using methods such as an auto/manual airbrush or compressor system.

The shape of the painted pattern can be controlled by the masking technique whereby a barrier or mask can be used to block the paint from the paintbrush. For example, a high precision barrier, with certain designed shapes, can be made in large quantities by using laser cutting into a stack of paper that has temporary adhesives on one side. Each sheet of barrier after the cut can be adhered onto a slab or slice before painting the slab or slice.

Figure 8A:
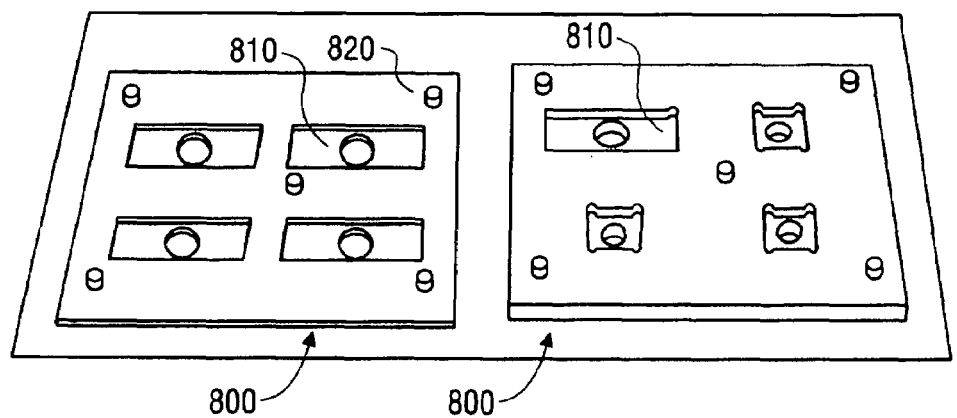
FIGS. 8A–8B illustrate embodiments of a painting device.
Figure 8B:
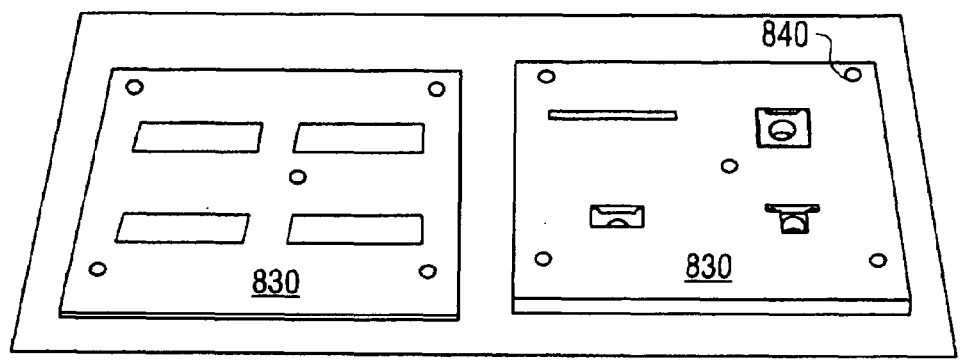

To paint the slab or sandwich slice, the object to be painted is placed into a painting device such as 800, as shown in FIG. 8A. It has recesses 810 which have a depth equal to the thickness of the slab or sandwich slice. It also has alignment pins 820 to accurately set a laser-trim painting barrier 830, which as discussed before, may be paper barriers with temporary and removable self-adhesive on one side, on it to precisely cover a part of the slab or sandwich slice, as shown in FIG. 8B.

The barrier 830 has laser-trim alignment holes 840 to match the alignment pins of the jig. A roller can be rolled over the mask to ensure that the mask is completely glued to the painting apparatus 800 and the slab or sandwich slice. The optical mask will then be applied over the masked jig containing the slabs or sandwich slices.

The patterns that these barriers 830 help to make on the crystals control the amount of scintillation-light signal going from one crystal to the next. It serves multiple purposes. It is a partition to block light transmission between crystals. It determines the degree of optical coupling or transmission between crystals. It is also a light-guide to guide the light distribution.

Advantages Over Conventional Methods

On average for making one 8×8 detector array, there are 12.25 painting of slabs, 8 cuts, and gluing of 14 surfaces together, for a total of 34.25 steps. This process can be compared with a detector block made by 64 individual elements, which requires 74 paintings and 119 surfaces or facets to glue, for a total of 193 steps. Therefore, the production process is greatly simplified with the proposed slab-sandwich-slice method.

The SSS production method also substantially increases the percentage-yield of good detector-blocks. Each type-A sandwich 501 (25 element long) yields more than enough slices for six blocks (4 slices per block×6 blocks=24 elements) and each of type-B 502 and type-C 503 sandwich can be used for 12 blocks.

Since all 25 slices cut from one sandwich are identical, if one bad cut breaks one slice, due to worn blade or crystal defect, the next cut may be used to replace the broken one. Hence, ⅛ of a block is wasted with one bad cut.

Figure 6:
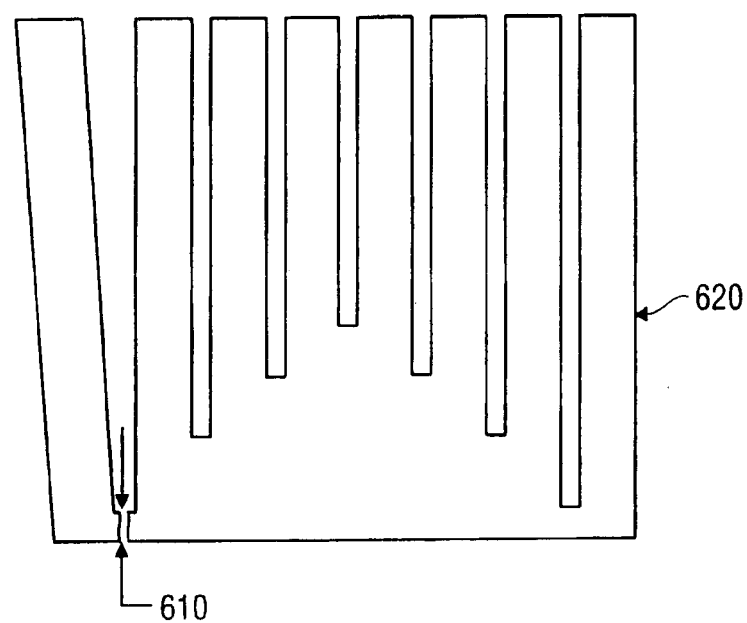
FIG. 6 illustrates the prior-art uneven-cut scintillation crystal block, and shows where the end crystals can break off easily.

In the first conventional production method described earlier, breakage and yield are much worse for two reasons: (a) The detector block 620 is crosscut as shown in FIG. 6, where the depth of the cut is very deep at the ends of the block, i.e., the small amount of material left is very small so it breaks easily 610, and (b) if there is one break, the whole detector block (64 crystal elements) 620 is wasted.

In one embodiment of this invention, however, all the cuts are complete clean-cuts without the small amount of crystal material for connecting to the adjacent elements. Hence, there is less breakage, which in turn, makes the finished detector approximately 50% more effective.

With this new production method, the same number of breaks would lead to an approximate loss of 4% or a 96% good-detector yield. Since the breakage will also be substantially lower as complete cuts are being made, the expected detector yield may be approximately 98% or better, which would lower the detector production cost substantially in both material and labor.

The slab-sandwich-slice method also may result in higher detection sensitivity and high position-decoding accuracy, which translates to better image resolution in the final imaging instrument that is produced using the detector arrays produced by said method. This method increases the finished detector yield by 50% to 150%, more commonly 50%, which would in turn reduce the cost of a large detection system. The invention improves quality and reduces costs compared to previous approaches.

Apparatus Using Position Sensitive Block Made by SSS Method

Recent approval by CMS (formerly HCFA) for reimbursement of PET scans used in certain cases of diagnostic oncology, and the rapid grow of the PET market that this approval has generated (100% increase in year 2000) creates the need for more affordable dedicated PET scanners. The manufacturing method discussed earlier was used in the development of a position sensitive block with the same detector area (40 mm×40 mm) and number of crystals (8×8) of the block of a commercial camera using the photomultiplier quadrant sharing technique (PQS).

Figure 9A:
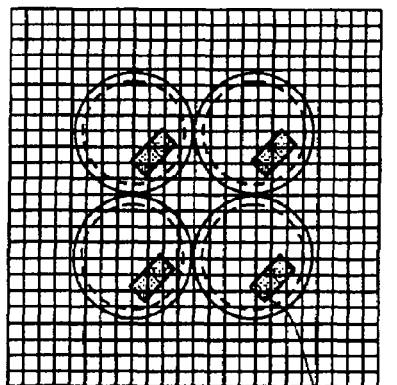
FIG. 9(A) illustrates a MDAPET quadrant sharing design; (B) a commercial camera detector design; and (C) an inexpensive 40×40 mm$^2$ block using PQS and 40 mm diameter PMT.
Figure 9B:
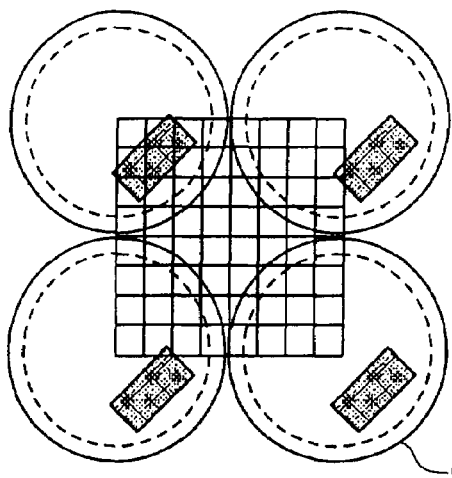
Figure 9C:
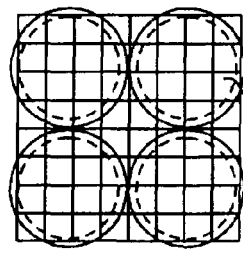

This block is coupled to four single-anode 40 mm diameter PMTs and each PMT is shared by four block detectors. Significant savings come from the number of PMTs required which are approximately 25% of what otherwise would be necessary to build a comparable commercial camera. One objective here is the development of a position sensitive block with the same detector area and number of crystals as the commercial block (64 crystals; as shown in FIG. 9C) but implemented in PQS mode, as shown in FIG. 9B. Rather than keeping the same PMT type 910 and reducing the block size, as shown in FIG. 9A (MDAPET implementation), the block dimensions remained the same, and the PMT type was replaced with a 40 mm diameter tube 920 as shown in FIG. 9B. One 40 mm circular PMT 920 replaces 4–19 mm PMTs 910, i.e. 75% savings in PMT alone.

Asymmetrical Position Sensitive Block

Due to unused photocathode area left by a PQS array of square blocks in a detector module, a rectangular (extended) block was developed. This block maximizes use of the PMT sensitive area and minimizes gap size between modules.

White-paint masks applied with accurate templates and airbrush were fine-tuned for every pair of adjacent crystals. Crystal decoding presents good separation uniformly distributed over the two-dimensional decoding map of the block. A composite energy spectrum of all 64 crystals would show a prominent photopeak (39% energy resolution) and a relatively small Compton component. It indicates that the block has a very uniform light collection for all crystals. It is expected that the image resolution using this type of block would be comparable to the resolution of commercial cameras because the same number and size of crystals are decoded.

Figure 10A:
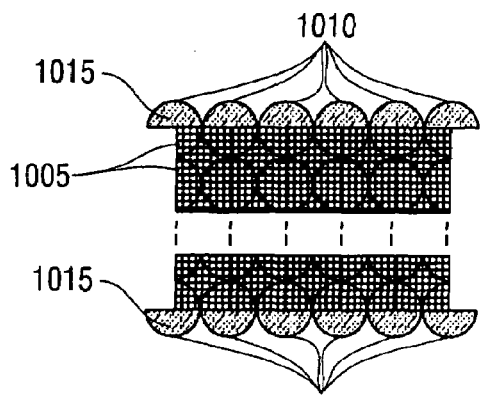
FIGS. 10A and B illustrate PQS designs showing unused PMT windows (shaded area). The circles=PMTs and squares and rectangles=block detectors. (A) Illustrates a design using only symmetrical blocks, (B) Illustrates a design using an embodiment of the invention.
Figure 10B:
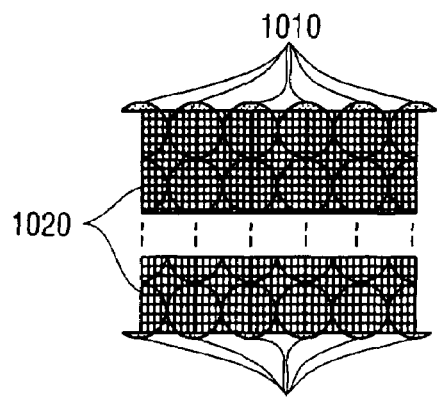

Quadrant Sharing implemented exclusively with square block detectors 1005 leaves unused one half of the sensitive window 1010 of the PMTs 1015 at the edge of the detector, as shown in FIG. 10a. It is sufficient to develop the rectangular detector type 1020, which may have a light guide or painted mask pattern that is situated asymmetrically with respect to the central axis of the detector array, in order to obtain both rectangular and symmetric blocks required for one detector module, as seen in FIG. 10b. The reason being, scintillation-light partitions placed between crystals that control light distribution across the short dimension of the rectangular block are exactly the same partitions for the symmetric square block 1005. The rectangular block developed for the 40 mm diameter PMT contains 8×8 crystals, each crystal is approximately 5.0 mm long by 6.3 mm wide by 25 mm tall making up a block 40×50×25 mm³. The height of the crystals was selected with enough length to ensure good sensitivity (three half-value layers) but not so long as to compromise image resolution due to paralax error. This block detector is intended for both whole-body as well as brain/breast scanners with the detector modules configured in a smaller diameter polygon.

Figure 11:
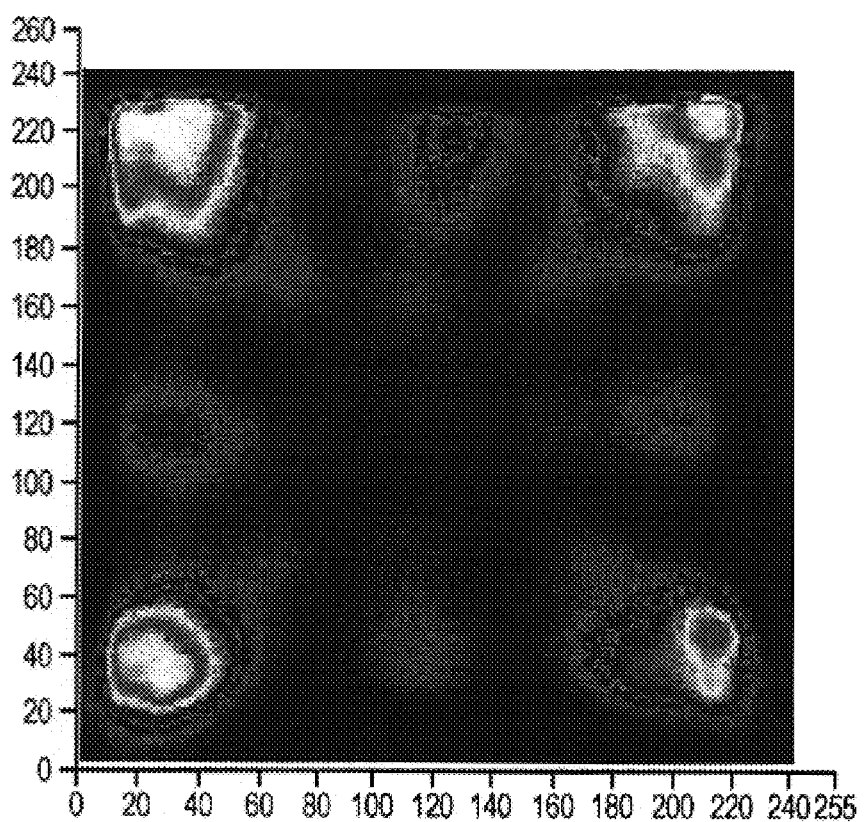
FIG. 11 illustrates a two-dimensional position-decoding map of a rectangular BGO block, an embodiment of the invention. All crystal surfaces are polished.

Giving special finish to the crystal surfaces helped to control light transmission from crystal to crystal and ultimately to the four PMT photocathodes. Contrary to the common objective of achieving maximum light output from each individual crystal at the output end of the crystal by providing polished surfaces to every crystal, which degrades crystal decoding, as shown in FIG. 11, the PQS block technique requires higher level of light transmission between crystals. Lapped crystal surfaces increase the light transmission between crystals and improve the two-dimensional crystal decoding, as shown in FIG. 12.

Crystal Position Decoding

In order to test the crystal position decoding of the experimental block, it was optically coupled to four 40 mm diameter Hamamatsu R580-15 photomultipliers using optical grease. PMTs gain were balanced using a single BGO (bismuth germanium oxide) crystal and $^{137}$Cs for gamma ray source. Adjusting the front-end electronics amplifier gain equalized Photopeak position of each PMT.

Figure 13:
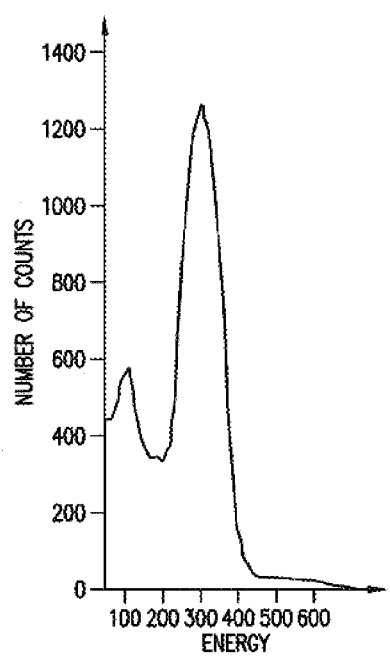
FIG. 13 illustrates a composite energy spectrum of all 64 crystals in the block, an embodiment of the invention.
Figure 12:
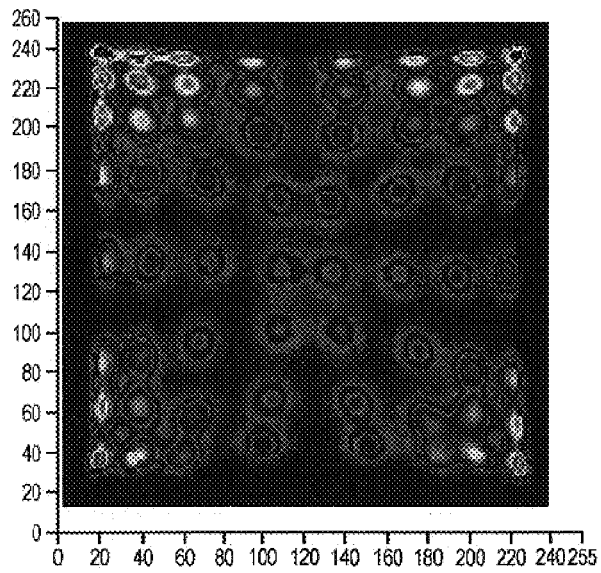
FIG. 12 illustrates a two-dimensional position-decoding map of a rectangular BGO block, an embodiment of the invention. All crystal surfaces lapped except for optically coupled surfaces that are polished.

FIG. 12 shows the two-dimensional position decoding map of the new block. Each element is clearly separated and evenly distributed over the map. FIG. 13 shows the composite energy spectrum of all 64 crystals in the block shows a prominent photo peak and relatively small Compton component. It indicates that the block has a very uniform light collection for all the crystals despite the asymmetric positioning of the block relative to the center of the four decoding PMT.

Circular Detector Array Design

Figure 14:
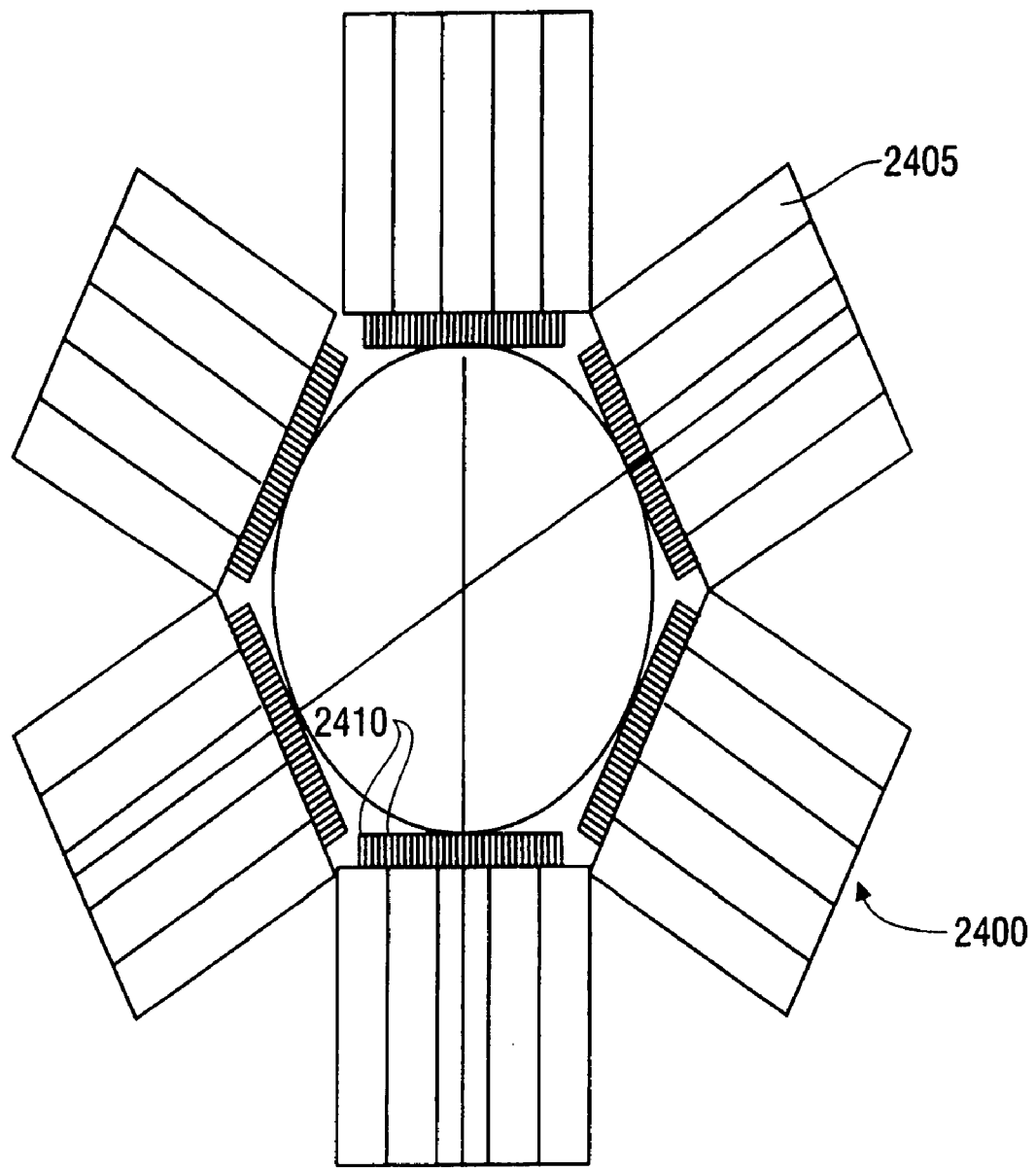
FIG. 14 illustrates a panel-based implementation of a detector array.

The scintillation crystal blocks created by the SSS method may be further modified to create detectors suitable for placement in a ring/circular detector array that may be utilized in apparatus such as a gamma ray camera. With the PMT-quadrant sharing design, the easiest PET implementation is to put many arrays/blocks into a large detector panel and put many panels circumscribing the patient in a polygonal pattern as shown in FIG. 14, which illustrates a polygon design with six detector panels 2400 comprised of PMTs 2405 and scintillation crystal blocks 2410. This panel-based implementation is easier for engineering/production, but it has its drawbacks.

Figure 15A:
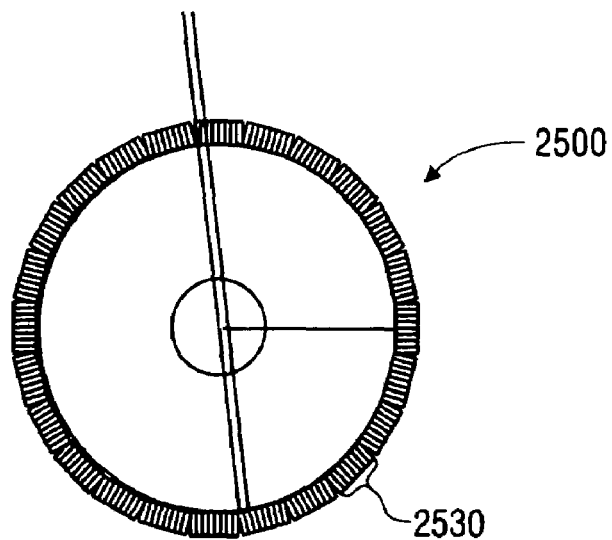
FIG. 15 illustrates incident rays in the circular and the panel-based implementations of a detector array.
Figure 15B:
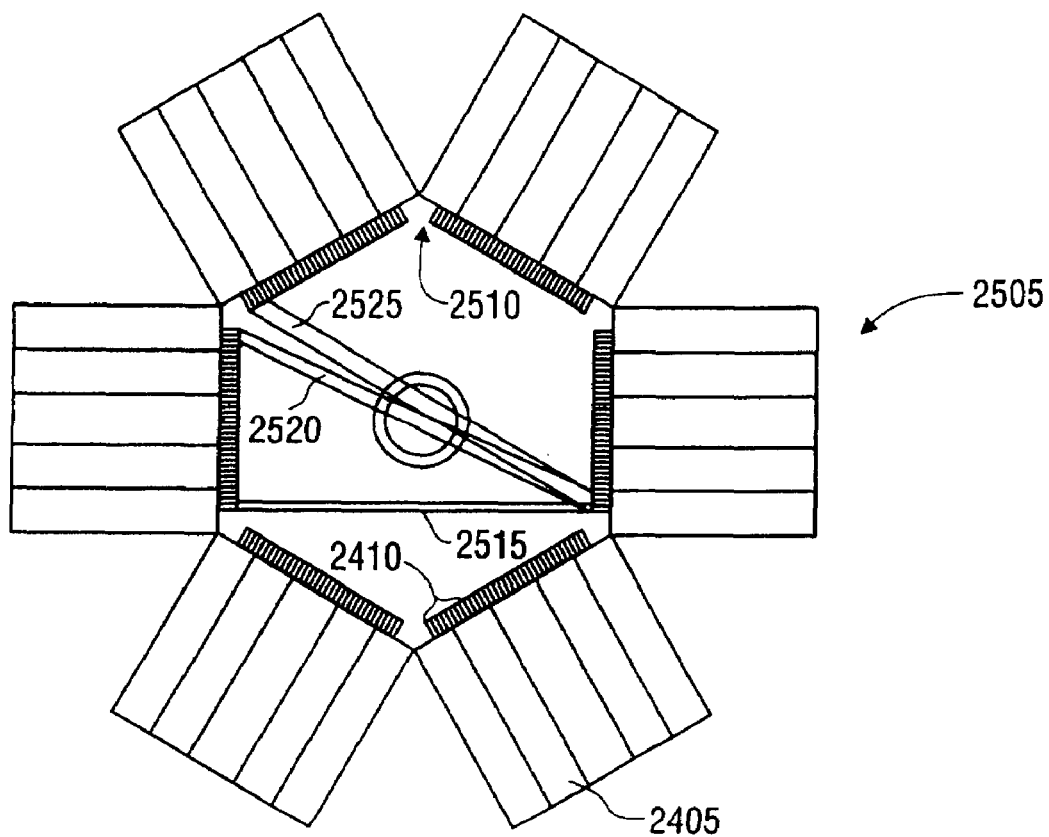

One of the drawbacks of the panel-based implementation is that the polygon design 2505 requires more crystals 2410 and PMTs 2405 than a circle design 2500 for the same imaging-port opening, as shown in FIGS. 15A and 15B, respectively. If the crystals 2530 are laid-out in the shape of a perfect circle 2500, fewer scintillation crystal blocks 2410 and PMTs 2405 are needed, thereby reducing production cost.

Another drawback that is shown in FIG. 15 is that there are detector gaps 2510 between panels/modules in a polygonal system. Therefore the system has to rotate during imaging to cover the detector sampling gaps. A continuous circle would eliminate the gap, hence obviating the need for rotating to save cost as precision stepping-motor control systems are not cheap and the data acquisition is more complex to rotate the system to keep track of the detector position in real time.

The image resolution is also better for a circular system 2500. In the polygon system 2505, even though the detector-pair width is 2.305 mm for the straight up-down ray 2515, for the oblique rays 2520, 2525, the 'effective' detector widths are widened greatly to 6.445 mm and 7.117 mm in the illustration because of the angulation of the crystals with respect to the rays from those events penetrating the adjacent crystals and hitting the tail of the target crystal. For the circular system, the effective widening is smaller due to less detector angulation. Hence, the more circular the system is, the better the average image resolution.

Another advantage of the circular implementation versus the panel-based implementation is that at the 4 edges of a detector panel/module, half a row of PMT is wasted, as they are not coupled with any crystals in the PMT-quadrant-sharing design, thereby reducing the cost advantage of the quadrant-sharing design. A continuous detector-ring implementation may eliminate this PMT waste in the in-plane circular dimension. Therefore, combining the quadrant-sharing ring implementation and the asymmetric solution (on the axial side) will be the best solution.

Figure 16:
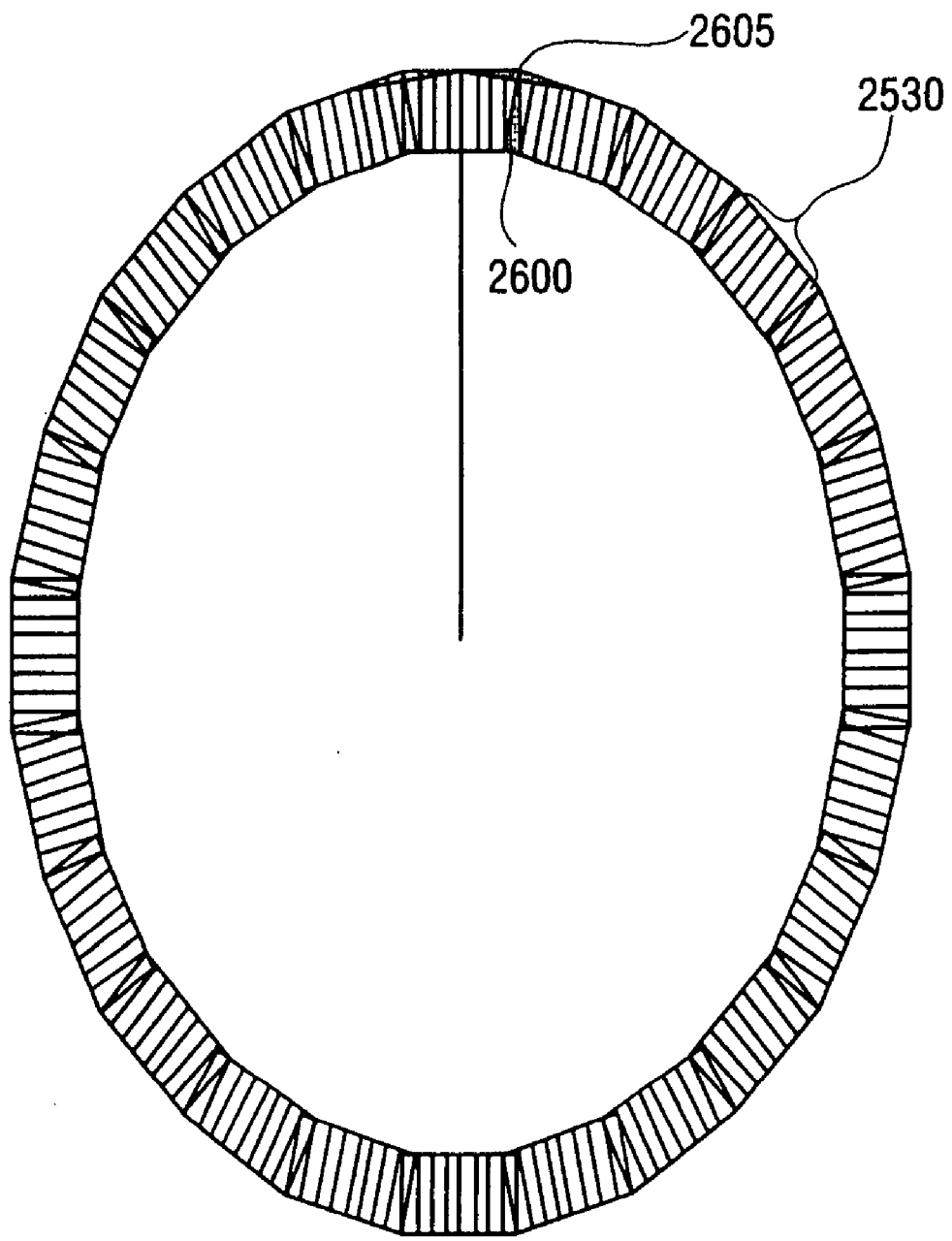
FIG. 16 illustrates the areas on the detector block that would need to be removed to implement a circular detector array.

For the cubical block produced in the slab-sandwich-slice production method (SSS) to be put into a more circular ring, there will be overlaps 2600 between blocks, which have to be ground off (FIG. 16). A second grounding 2605 is necessary to adopt the PMT-quadrant-sharing design for the flat detection window of a PMT thereby making the block into a pentagonal block.

Figure 17A:
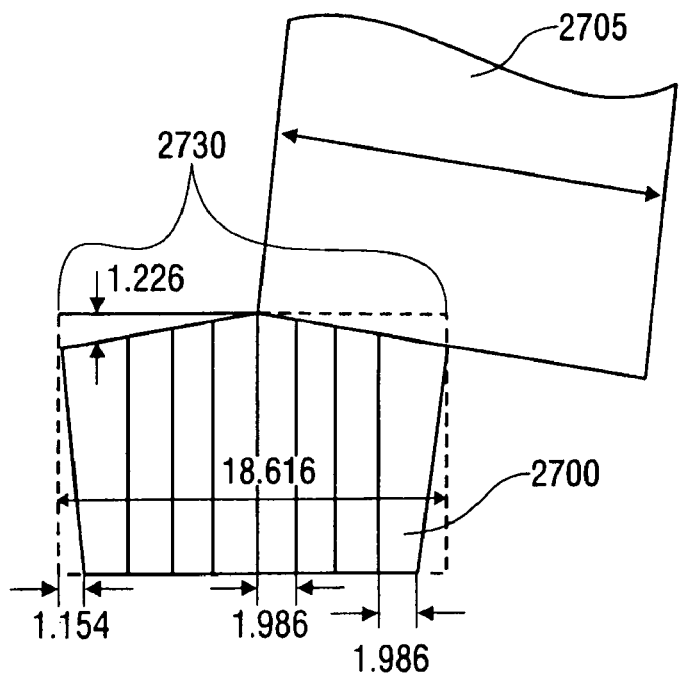
FIGS. 17A–17B illustrates two ways to design the detector block used in a circular detector array.
Figure 17B:
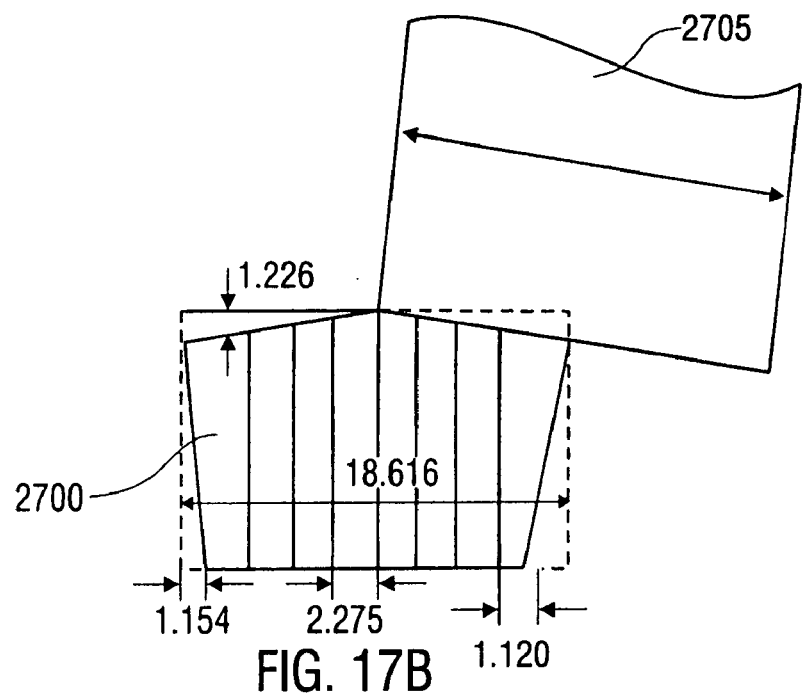

There can be two ways to implement the pentagonal block 2700 in relation to PMT 2705 that is shown in FIG. 17 from the SSS produced block: (1) equal-entrance-width crystals (FIG. 17A) and (2) equal-back or equal-production-slice thickness crystals (FIG. 17B). The equal-entrance-width implementation would require cutting thicker slices for the 2 end-crystal-rows of the pentagon in the slicing operation in the SSS production. The equal-back implementation may need just the regular spacing slicing. The equal-entrance would make the spatial resolution more uniform across the block and the camera specification more attractive as the crystal aperture is smaller (1.986 mm in the example compared to 2.275 mm and 1.12 mm for the equal-slice example in FIG. 17B). Certainly, these are examples of limit boundaries that may be used. Crystal divisions that fall between these limit boundaries may also be used.

The small grinding shown (1.154 mm for the block overlap and 1.126 mm for the PMT-quadrant sharing) is already an extreme large grinding distance for a very small animal PET (mouse PET) with a detector ring diameter of only 12.7 cm. For a human camera with a larger detector ring diameter, the grinding needed will be smaller.

Figure 18:
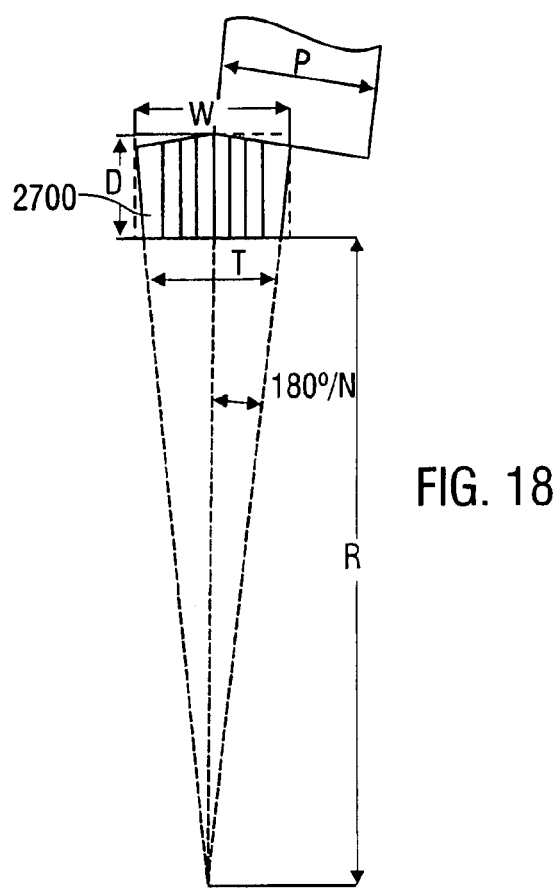
FIG. 18 illustrates the dimensions of the detector block needed for shaping of the detector block for inclusion in a circular detector array.

The formulae governing the tapering of the block overlap (T) and the grinding of the pentagonal shaped blocks are given here. Assuming that N is the number of blocks to make the circle, that W is the pre-grinding dimension of the finished block, D is the depth (thickness of the block), P is the photomultiplier pitch/space, R is the radius of the detector ring, and T is the tapering of the block as shown in FIG. 18.

$$W = P \cos(180°/N)$$

$$R = W/\sin(360°/N) - D$$

$$T = W/\cos^2(180°/N) - 2D \tan(180°/N)$$

The "roof" (e.g. the sides of the pentagonal block 2700 coupled to the PMT 2705 as seen in FIGS. 17A and 17B) grinding is 180°/N from the mid-line of the top side of the block.

Figure 19A:
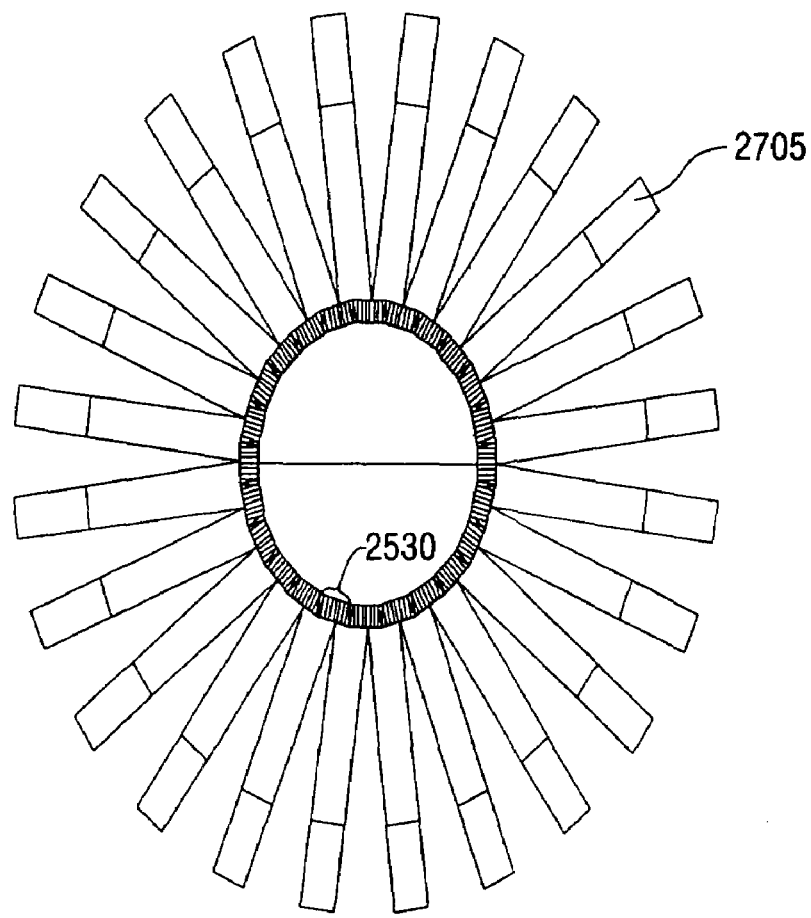
FIG. 19 illustrates a circular detector array that does not use asymmetrical detector blocks.
Figure 19B:
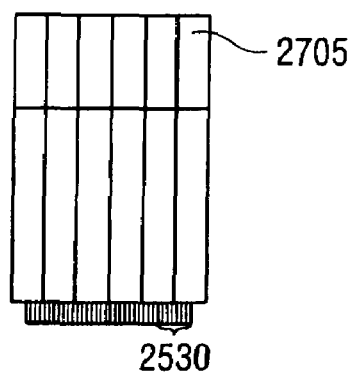
Figure 20A:
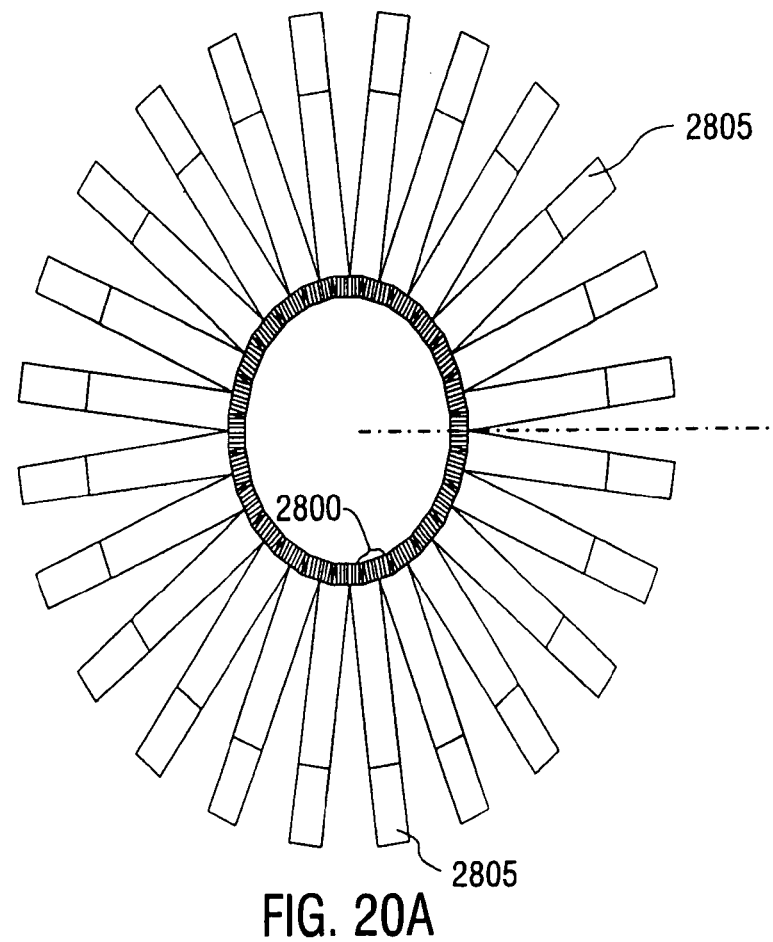
FIG. 20, illustrates a circular detector array using asymmetrical detector blocks, in accordance with an embodiment of the invention.
Figure 20B:
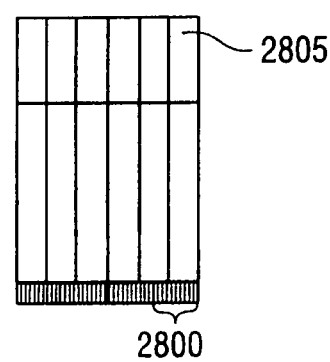

After the implementation, the regular PMT-quadrant sharing circular system with PMT 2705 and scintillation crystal blocks 2530 may be implemented in a system similar to the one shown in FIGS. 19A and 19B. A system with asymmetric elongated scintillation crystal end-blocks 2800 in the axial dimension and PMTs 2805, in a circular system may be implemented in a system similar to the one shown in FIG. 20.

In this circularized-block design, the end crystals may have different sensitivity compared to the inside crystals. The sensitivity difference may be easily corrected by software in the image reconstruction process as detector-sensitivity correction always exists in any PET camera. This additional variation may be corrected at the same time.

PET Camera

A very high-resolution PET camera has been designed using detectors made from the method describe above. This system was designed to provide high versatility for both clinical and research applications. The camera can be transformed into different operating modes: a regular human wholebody PET, an extra-large radiotherapy treatment planning system, a high sensitivity dedicated brain system, and a high sensitivity dedicated breast PET, a high sensitivity small animal PET.

The expected intrinsic image resolution may be approximately 2.5 mm for regular wholebody cancer staging and approximately 2.2 mm for murine imaging. The system is designed for the purpose of testing the usefulness of ultra-high resolution PET for different dedicated applications in both research and clinical environments. The system is also designed to minimize the potentially high-production cost of very high resolution PET cameras.

The system uses a modular design to provide the necessary flexibility to facilitate a transformable architecture. HOTPET (high-resolution oncologic transformable PET) utilizes a novel transformable geometry that can alter the detector-ring diameter from approximately 24 cm to 100 cm. The detector ring is made of 12 detector modules. Each detector module is independent and has a rectangular detection area (13×21 cm$^2$). In the regular wholebody scanning PET mode, the detector ring diameter is approximately 83 cm with no gap between detector modules and an axial field of view (AFOV) of approximately 13 cm. In this regular wholebody mode, the camera has 44 detector rings imaging 87 planes/slices with a slice to slice separation of approximately 1.4 mm. This imaging mode is used for wholebody cancer staging and cardiac applications as in regular commercial PET.

Figure 21:
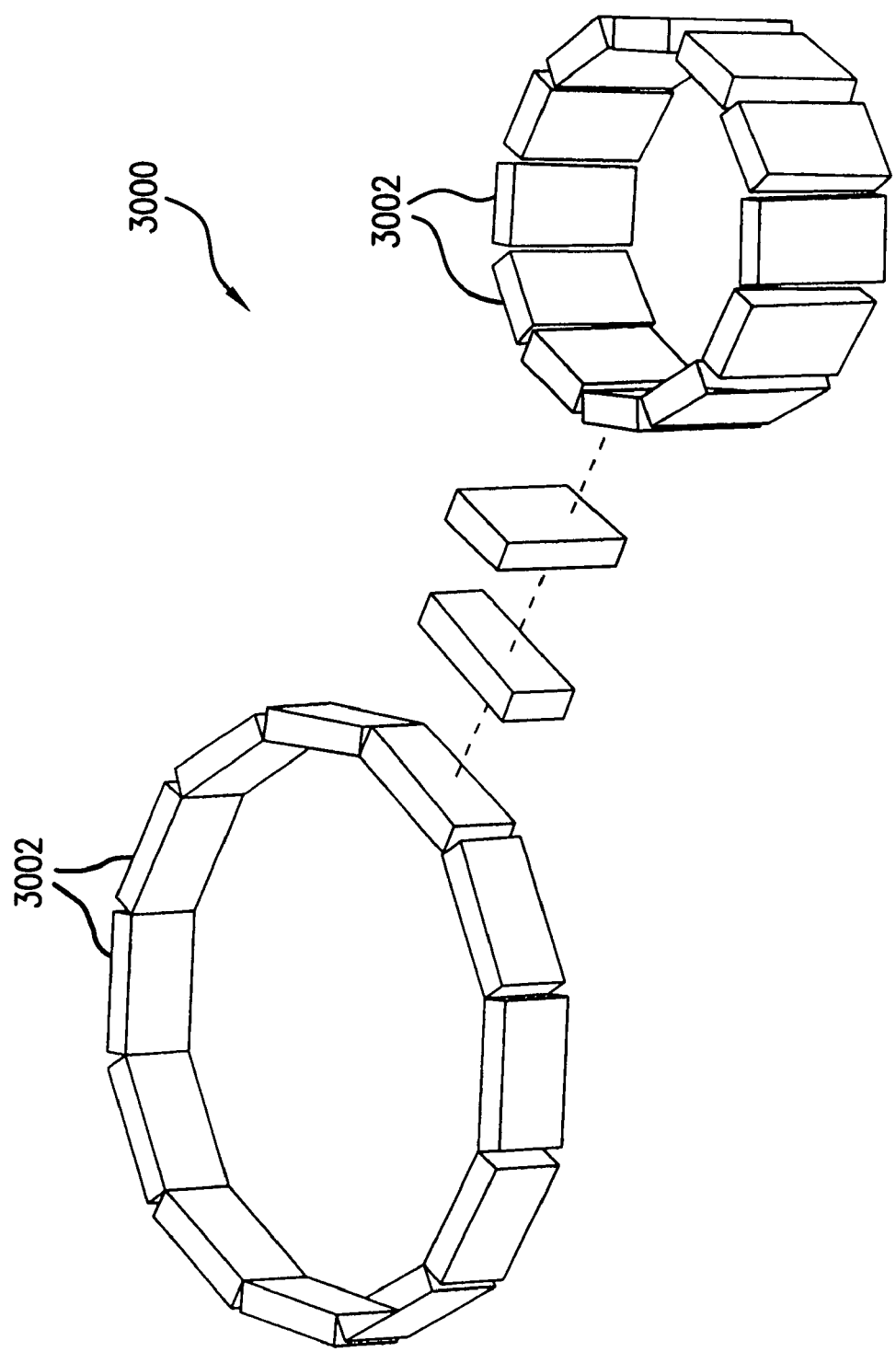
FIG. 21 illustrates a basic transformation design of a PET camera which uses an embodiment of the invention.

Secondly, modules 3002 of detector ring 3000 can rotate 90° about their individual axis, so a transaxial-row of detectors becomes an axial-column as shown in FIG. 21. After this rotation and a radial displacement inward, the detector-ring diameter becomes 53 cm with a very large axial-FOV of approximately 21 cm. This small diameter mode can change the camera into a dedicated brain and breast PET with very high resolution and sensitivity. This brain/breast mode has 72 detector rings imaging approximately 143 planes/slices simultaneously. The 3-D coincidence sensitivity in this mode increases by approximately 4 times from that of the regular wholebody mode (83 cm) because of an approximate 62% increase in AFOV and an approximate 57% decrease in ring diameter. The intrinsic resolution may also improve from 2.6 mm to 2.2 mm by reducing annihilation non-collinearity effect. This very high resolution and sensitivity design is very beneficial for brain imaging. For breast imaging, without the body to attenuate the signal, there is another approximately 5 times increase in sensitivity, for a total of approximately 20 times higher sensitivity over a regular clinical PET, which when coupling to a 2.2 mm intrinsic resolution, would potentially allow very small breast lesions with lower tracer uptake to be detected.

The ring can be expanded from 83 cm to approximately 100 cm by displacing the modules radially outward thereby creating an 80 cm patient port so that the system can be used as a radiotherapy treatment-planning PET. This creates small detection gaps of approximately 17% between detector modules, which is acceptable without causing image artifacts, if the gantry can rotate 15–30°. The system is designed to rotate 30°. In this radiotherapy treatment-planning mode, the system also has 44 detector rings imaging 87 planes/slices with a slice-to-slice separation of 1.4 mm.

The camera can also be transformed into small animal PET with detector diameters of 41 cm and 24 cm, by using 4 or 6 of the detector modules. In the 24 cm mode (6 modules), coincidence non-collinearity is minimized to yield an intrinsic resolution of approximately 2.0 mm for imaging mice and rats. Since the animal mode has 21 cm axial-FOV, it has approximately 7 times higher coincidence sensitivity over a mouse PET with 8 cm AFOV in 3-D acquisition.

Inside each detector module, each scintillation crystal is separated from its neighboring crystal by a very small gap of approximately 0.04 mm. This small inter-crystal spacing provides a very high detector-packing fraction of approximately 98.5% for both the axial and transaxial dimensions. Coincidence-sensitivity is proportional to the (area packing fraction)2 or (linear packing fraction)$^4$. Hence, comparing to a regular detector design with a normal packing fraction of 90%, the HOTPET detectors has an approximate $(98.5/90)^4=1.43$ times increase in coincidence-sensitivity. This allows the axial-field-of-view (AFOV) to be decreased from the 15 cm in the regular commercial BGO PET to 13 cm without sacrificing coincidence-detection sensitivity. In 3-D imaging acquisition, the coincidence sensitivity is proportional to AFOV$^2$. Hence, the 1.43 times higher sensitivity coming from the very high detector packing fraction allows the decreasing of the AFOV from the regular 15 cm in dedicated clinical BGO PET to 12.5 cm with no loss in sensitivity. Decreasing the AFOV by 2 cm in the design reduces the number of PMT, BGO and electronics by 1/8 or 12.5%, which would lower the production cost of the camera without sacrificing detection sensitivity. Furthermore, the narrower wholebody AFOV of 13 cm in this design also allows the lead-shields (on either sides of the detector ring) to block scatter and accidental events more effectively than a regular 15 cm AFOV, thereby improving image quality and noise-equivalent sensitivity in septa-less 3-D imaging. Hence, the high detector-packing fraction design would lower production cost and improve image quality at the same time.

A second-generation PQS detector design can be used in this camera, instead of the first generation PQS design in the prototype MDAPET that achieved an approximate 2.8×3.4 mm image resolution (transaxial×axial) using 19 mm PMT. In the first generation PQS development, two light-distribution design methods were tested, the sawed grooves technique and a painted mask technique. 128 BGO detector blocks/arrays were built, where all the arrays along one dimension were saw-cut while along the other dimension, painted masks were used. The arrays were installed into the MDAPET prototype platform with all the sawed-grooves along the transaxial direction for defining the axial resolution and with the painted-masks along the axial direction for defining the transaxial resolution. The image resolution on the prototype was measured. The painted-mask direction (transaxial) were found to have an approximate resolution of 2.8 mm while that of the sawed-groove direction (axial) had an average approximate resolution of 3.4 mm. Since these resolution measurements were the combined effect of 128 detector arrays (6272 crystals), this finding showed that the painted-mask method should achieve a higher image resolution as compared to the sawed-groove method.

This increase in coincidence-detection efficiency derived from the painted mask is used to advantage in lowering the production cost of the camera, and to reduce the scatter and accidental coincidence noise by decreasing the axial field-of-view from the typical 15 cm to 13 cm. This decreases the detector components by 1 PMT ring (saving approximately 132 PMT and 6048 BGO crystals).

Figure 26:
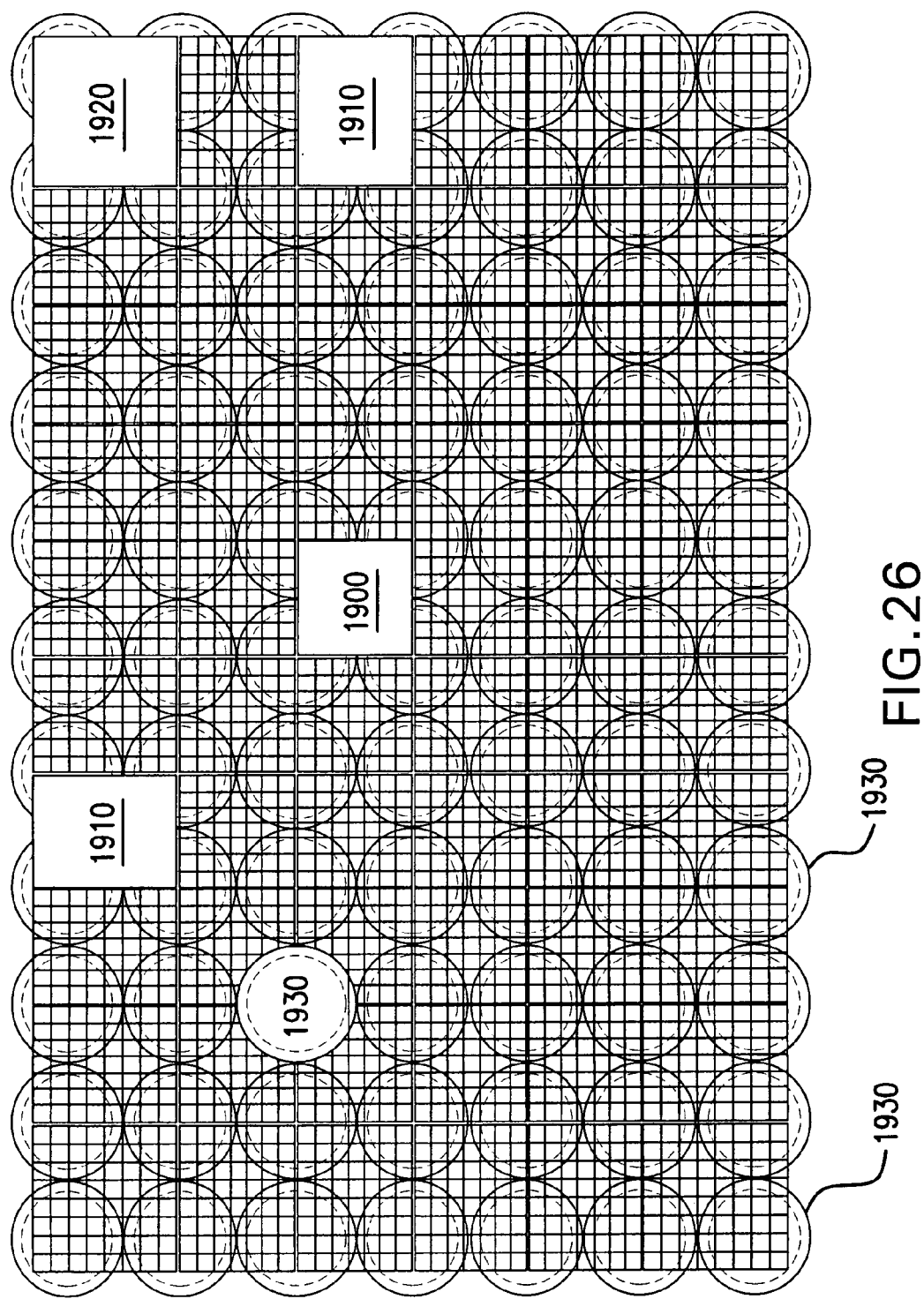
FIG. 26 illustrates a detector module design with PQS asymmetric edge and corner arrays, an embodiment of the invention.

The detector module design is shown in FIG. 26. In addition to using the regular PQS detector design 1900, the detector module also uses elongated asymmetric PQS-array designs along the edges 1910 and corners 1920 of each detector module to increase the usable crystal/detector areas of the PQS detector modules. In this implementation, 7×7 detector arrays 1900, made with the regular PQS detector design, are located in the middle of the detector module and enclosed by asymmetrical detector arrays. The detector arrays along the edge 1910 of the detector module are 7×8 arrays, while the detector arrays at the corners 1920 of the module are 8×8 arrays. Without the elongated asymmetric PQS-array designs, half a row of PMTs 1930 would be wasted on each of the 4 edges of a detector module. A set of asymmetrically placed masks can be used for the edge and corner detector arrays.

Figure 27:
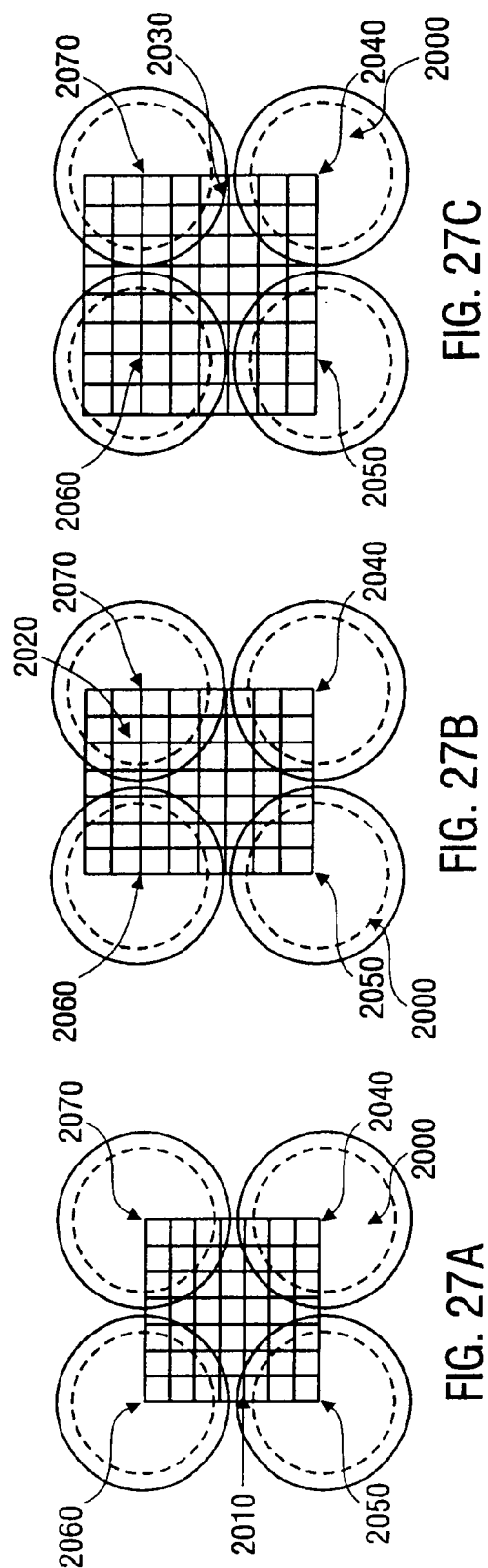
FIG. 27 illustrate embodiments of the invention.

The different PQS detector designs are shown in FIG. 27. Each one of the three types of detector arrays shown 2010, 2020, 2030 are displayed in relation to a grouping of 4 PMTs 2000. In the 7×7 detector array design 2010, the detector 2010 is of a regular PQS design with the array centered in relation to the PMTs 2000 and each of its four corners is aligned with the center of a PMT 2040, 2050, 2060, 2070. Thirty-two arrays of this type of detector array were used in the detector module depicted in FIG. 26.

In the extended 7×8 detector array 2020, an asymmetrical detector array design was used. This array 2020 is not centered relative to the grouping of 4 PMTs 2000, and only two of its corners are aligned with the centers 2040, 2050 of the PMTs in the grouping. When placed into a detector module, these two corner edges 2040, 2050 may be aligned with the corner edges of other scintillation crystal arrays that are aligned to the one or both of the same corner(s) 2040, 2050. The remaining two corners extend past the remaining PMT centers 2060, 2070. The 7×8 detector array 2020 can be said to be asymmetrical in one dimension. Twenty-four arrays of this type of detector array were used in the detector module depicted in FIG. 26.

In the double-extended 8×8 detector array 2030, another asymmetrical detector array design was used. This array 2030 is also not centered relative to the grouping of 4 PMTs 2000, and only one of its corners is aligned with a center 2040 of a PMT in the grouping. When placed into a detector module, this corner edge may be aligned with the corner of another scintillation crystal array that is aligned to the same corner 2040. The remaining three corners of the 8×8 detector array extend past the remaining PMT centers 2050, 2060, 2070. The 8×8 detector array 2030 can be said to be asymmetrical in two dimensions. Four arrays of this type of detector array were used in the detector module depicted in FIG. 26.

Figure 22A:
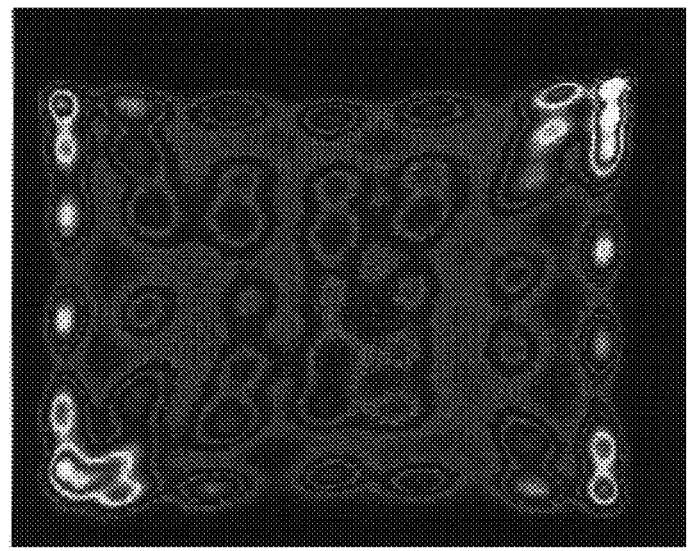
FIGS. 22A–B illustrate crystal decoding maps of (A) a prior art first generation PQS array and (B) a second generation PQS array that uses an embodiment of the invention.
Figure 22B:
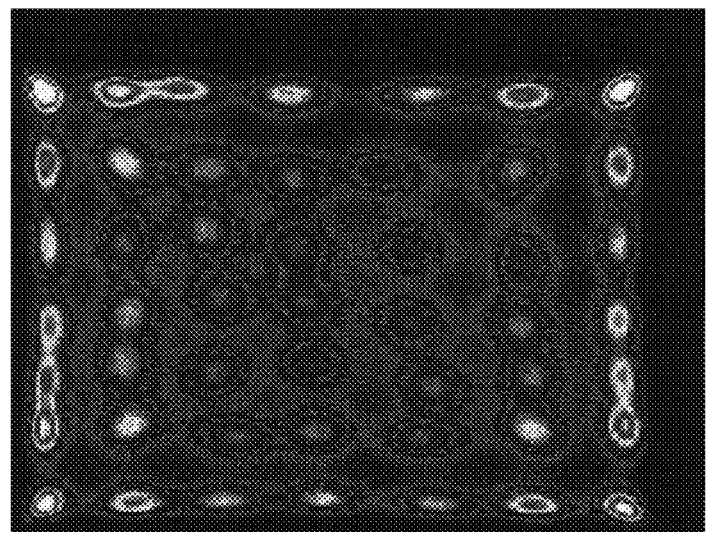

The second generation PQS detectors using the painted mask technique also improve on the position decoding of the individual BGO crystals in the detector array, as shown in FIGS. 22A and 22B, where FIG. 22A shows the first generation PQS detectors, and FIG. 22B shows the second generation PQS detectors.

Current PET cameras either operate in a 2-D image acquisition mode with a full set of inter-slice septa (lead or tungsten) or operate in a 3-D imaging mode with no septa in the AFOV (axial field of view). In the brain/breast/animal configurations, the system can be operated in the 3-D septa-less mode. In the wholebody configuration, an intermediate septa system can be used. The intermediate septa system allows 3-D data to be acquired while reducing the scatter and accidental coincidence noise. From Monte Carlo simulation studies, the intermediate septa system will have 5–7 septa spanning the 13 cm AFOV with a septum spacing of approximately 2 cm.

Figure 23A:
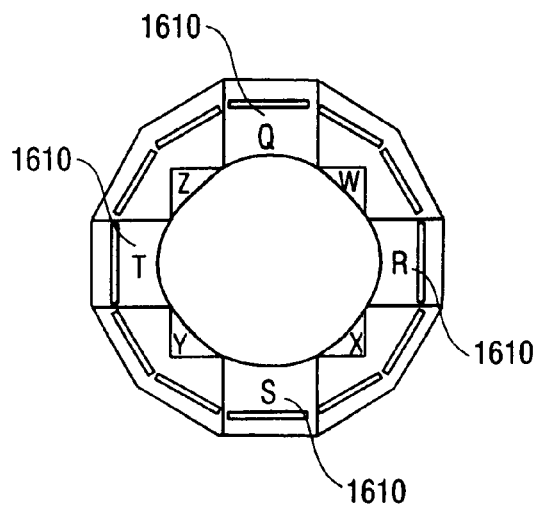
FIG. 23 illustrates an adjustable shielding design with sliding sections (Q, R, S, T) that uses an embodiment of the invention. Sections (W, X, Y, Z) can be flipped or placed manually for the small mode.
Figure 23B:
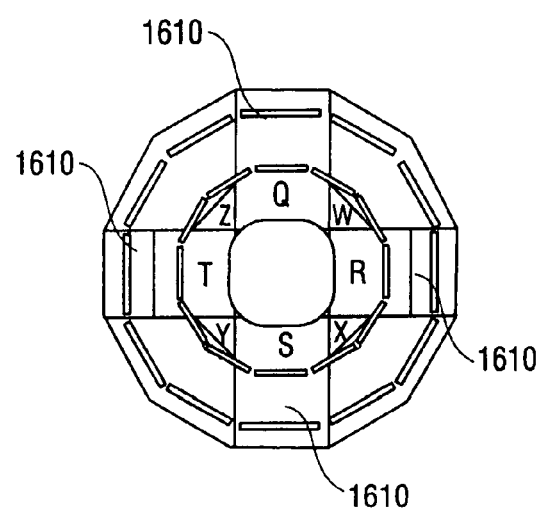

The thick lead shield on the back side of the detector annulus can be a lead annulus fixed at the wholebody mode with a patient opening of approximately 60 cm in diameter. The front lead shield (patient-entry side) has four opposing movable (sliding) sections (Q, R, S, T) 1610 that can be continuously positioned between the body opening and the brain/breast opening, as shown in FIG. 23. In the brain/breast mode, most of the patient's body (radiation) is outside the front shield, thus only the front shield needs to be adjustable and the back shield can be fixed to simplify the mechanics. This sliding front shield can also benefit body imaging because the patient body cross-section comes in different sizes and shapes. In the front shield, the four movable sections can slide to optimal positions, that is, as close to the patient as possible to block scatter/accidentals, depending on the section to be scanned and the size of the patient. Hence, optimal shielding tailored to the individual patient and study would be possible with this simple 4-section sliding front shield.

High-yield-pileup-event-recovery Electronics

The high-yield-pileup-event-recovery (HYPER) electronics that were recently developed to increase the count-rate performance of scintillation detectors may be incorporated into the front-end electronics of the camera. The HYPER electronics has been demonstrated to increase the count-rate or imaging rate of NaI(T1) by approximately 10 times and that of BGO by 6–8 times.

Figure 24:
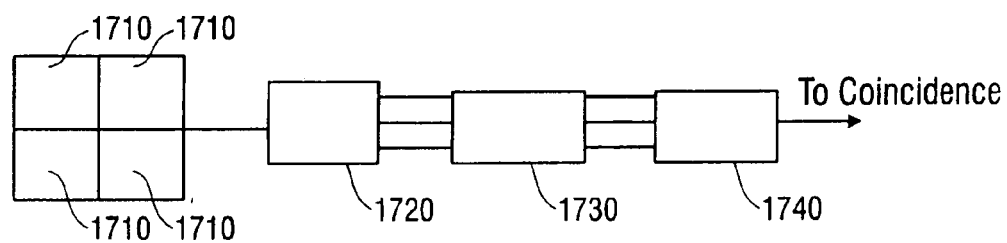
FIG. 24 illustrates an embodiment of the front-end electronic architecture for each detector module.

The electronic design is also modular like the detector system. The front-end electronics design for one detector module is shown in FIG. 24. All the crystal arrays in a detector module may be divided into 4 Anger-camera zones 1710 by Anger weighting the PMT signals according to their physical locations. The number of zones that the crystal arrays in the detector module may be divided into is variable. Each Anger-camera zone 1710 has one HYPER electronic board 1730 to do the real time data acquisition, thus a total of 48 HYPER circuits are used in the system. Since each HYPER circuit allows its BGO detectors to operate at approximately 800,000 events/sec, the system can process approximately 40,000,000 events/sec. This high count-rate, high-speed electronic design is also very low cost because 144 ADC are used for the 48 HYPER circuits in the whole camera that has 38016 crystals, 924 PMT and 720 crystal arrays. Fewer ADC also means fewer other affiliated electronics and smaller real estate. In a regular design, there may be one ADC for each PMT (a total of 924 ADC), or 3 ADC per array (X, Y, E) for a total of 2160 ADC.

The 4-Anger-camera circuit board 1720 depicted in FIG. 24 includes an amplifier for each PMT, the computer controlled auto-gain adjustment for each amplifier (with a PC parallel port interface to a monitoring PC), the PMT-position weighting circuit, and the high-voltage distribution for the PMT. The 4-Anger-camera circuit 1720 is a small board approximately 12×20 cm in size, placed inside each detector module.

The 4-HYPER circuit 1730 in FIG. 24 includes 4 HYPER daughter boards plugged into a multiplexer (4 to 1) mother board 1740 to generate one signal output for this detector module. The output signal includes the scintillation position (before energy normalization), the energy, and the timing-gate pulse for coincidence matching. The output signal is synchronized (but delayed by approximately 1.5 μsec) with the arrival of the event. All the outputs of the detector modules are sent to a modular coincidence board for coincidence matching.

The coincidence matching of events coming from different detector modules is performed by an AND logic on the time of arrival of the timing-gate in the module output signal. The use of the timing-AND logic for coincidence matching instead of using a time-stamp comparison is for minimizing the dead time in coincidence-matching. In the prototype MDAPET, a time-stamp matching design that has a dead time that is longer than desirable (80 ns) was used. The coincidence-match dead time of the new coincidence circuit is approximately 22 ns for an event-pair. The coincidence-timing window is adjustable between 9 and 30 ns. Both true and accidental coincidences are collected; the accidental timing shift is approximately 200 ns relative to the true events. All multiple coincidences (triple, etc) are rejected. There are 42 module-pairs of coincident combinations derived from the 12 detector modules. Each of the 42 module pairs are independently processed. The coincidence-matching circuit itself has a timing accuracy of approximately 0.5 ns.

Since the coincidence matching is performed by timing-AND logic for the arrival of the detector-module signal, the detector-module signal for each event (single) has to be synchronized to the triggering time (arrival time) of the event. However, the HYPER pileup-prevention circuit requires a dynamic integration of the scintillation charge (the integration stops at the random time of arrival of the next event). Hence, the arrival time of an event is not synchronized to its charge-integration-stopping time; this is unlike the current PET system that has a fixed integration period. This non-synchronization between the event-arrival time and the integration-stopping time would not normally allow the use of the timing-AND logic for coincidence matching.

The new HYPER pileup-prevention electronics has been tailored for BGO scintillation detectors to improve the resolution of the circuit. The improvement include a non-linear filter for the timing trigger circuit, a multiple sampling of the raw/total energy and position signals (including pileup signals).

Testing of the SSS Made Crystal Array

In order to test the crystal position decoding of the experimental block, it was optically coupled to four 40 mm diameter Hamamatsu R580-15 photomultipliers using optical grease. PMTs gain were balanced using a single BGO (bismuth germanium oxide) crystal and $^{137}Cs$ for gamma ray source. Adjusting the front-end electronics amplifier gain equalized Photopeak position of each PMT.

In the new block, each element is clearly separated and evenly distributed over the map. A composite energy spectrum of all 64 crystals in the block shows a prominent photo peak and relatively small Compton component. It indicates that the block has a very uniform light collection for all the crystals despite the asymmetric positioning of the block relative to the center of the four decoding PMT.

Extended block using four 40 mm PMT configured in photomultiplier quadrant sharing mode (PQS) and double-coat selected partitions was built. Using larger PMTs than the commercial cameras the new detector block will require ¼ the number of PMT while keeping similar imaging capabilities. Production cost can be reduced implementing the two-mask two-glue process (SSS) described earlier. Further reduction could come from assembling BGO crystals without polished optical surfaces. Then, in one operation, the entire face of the block can be polished.

Crystals with lapped surfaces may be important to achieve appropriate crystal decoding of position sensitive scintillator blocks using the Photomultiplier Quadrant Sharing technique. Image resolution is expected to be comparable to the resolution of commercial cameras because the same number and size crystals are decoded. In one embodiment, there is no need for a light guide in this block design, thereby cutting costs in both materials and assembly. However, in other embodiments, light guides may be used.

Figure 25:
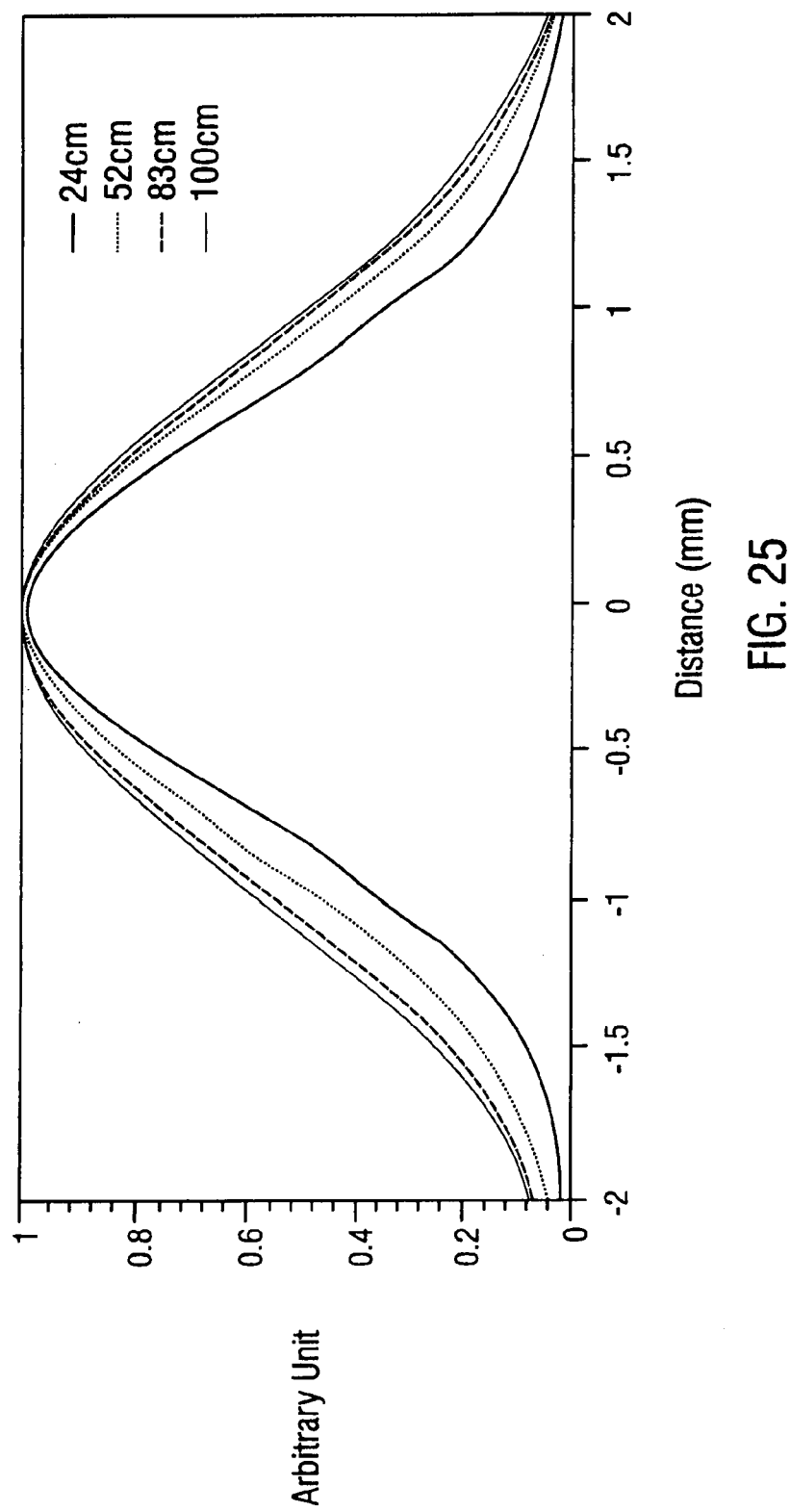
FIG. 25 illustrates Monte Carlo simulations of intrinsic spatial resolution of an embodiment of a detector array.

Monte Carlo simulation studies were performed to gauge the expected performance of this transformable PET camera. The simulation results included the effect of inter-crystal Compton scatters, photopeak-photopeak events, coincidence noncollinearity, light-sharing Anger-position decoding errors and the positron range of 18-F isotope. Excluding the effect of reconstruction blurring, the intrinsic spatial resolutions were simulated for the regular body mode (83 cm detector ring), the brain/breast mode (53 cm detector ring), the radiotherapy mode (100 cm detector ring), and the murine mode (24 cm detector ring). The results are shown in FIG. 25.

The basic design of a very high resolution, lower cost dedicated BGO PET camera with a transformable geometry has been presented. This camera has a transformable transaxial and axial fields-of-view to facilitate oncology applications and to enhance detection sensitivity for brain/breast imaging. The very high resolution human-body imaging mode (2.6 mm) would be useful for detecting smaller metastatic lesions than current clinical PET cameras for more accurate cancer staging. For brain imaging, the large 21 cm axial field-of-view, the smaller detector ring and the detector packing fraction of approximately 98.5% would provide a total of 4 times higher coincidence-detection sensitivity (in 3D) than a regular BGO clinical wholebody PET, which, when coupled to a potential 2.1 mm spatial resolution, would be a very useful brain imaging device especially for receptor studies and for the detection of recurrent brain tumors. For the breast imaging mode, very small breast lesions can be detected with the projected 2.1 mm resolution and an effective increase in coincidence-detection sensitivity by approximately 20 times compared to a wholebody PET; the imaging time would be very short due to its 20 times sensitivity enhancement, which would reduce patient movement artifacts and increase patient throughput. For murine imaging, a resolution of approximately 1.8 mm and a large 21 cm axial field-of-view would be useful for receptor studies as it can provide a 7 times higher sensitivity (3-D) compared to a standard mouse-PET with 8 cm AFOV.

Electronically, this PET camera can process 40 million singles/sec and has a coincidence dead time of 22 ns. As noted previously, 144 ADC are used for the whole camera. All the PMT gains in the system can be equalized in 2–3 minutes without using radiation and human intervention, which allows the whole system to be tuned for each patient to optimize image quality at all time.

A practical application of the invention that has value within the technological arts is to improve the production and performance of detectors for PET cameras. It can also be used to produce detector arrays for neutron position-sensitive detectors, airport and building bomb-detection systems, and custom-inspection systems for container trucks, freight trains, cargo containers and oil tankers.

The terms a or an, as used herein, are defined as one or more than one. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). A program, or computer program, may include a subroutine, a function, a procedure, an object method, an object implementation, an executable application, an applet, a servlet, a source code, an object code, a shared library/dynamic load library and/or other sequence of instructions designed for execution on a computer system.

EXAMPLES

Specific embodiments of the invention will now be further described by the following, nonlimiting examples which will serve to illustrate in some detail various features. The following examples are included to facilitate an understanding of ways in which the invention may be practiced. It should be appreciated that the examples which follow represent embodiments discovered to function well in the practice of the invention, and thus can be considered to constitute preferred modes for the practice of the invention. However, it should be appreciated that many changes can be made in the exemplary embodiments which are disclosed while still obtaining like or similar result without departing from the spirit and scope of the invention. Accordingly, the examples should not be construed as limiting the scope of the invention.

Example 1

Figure 28:
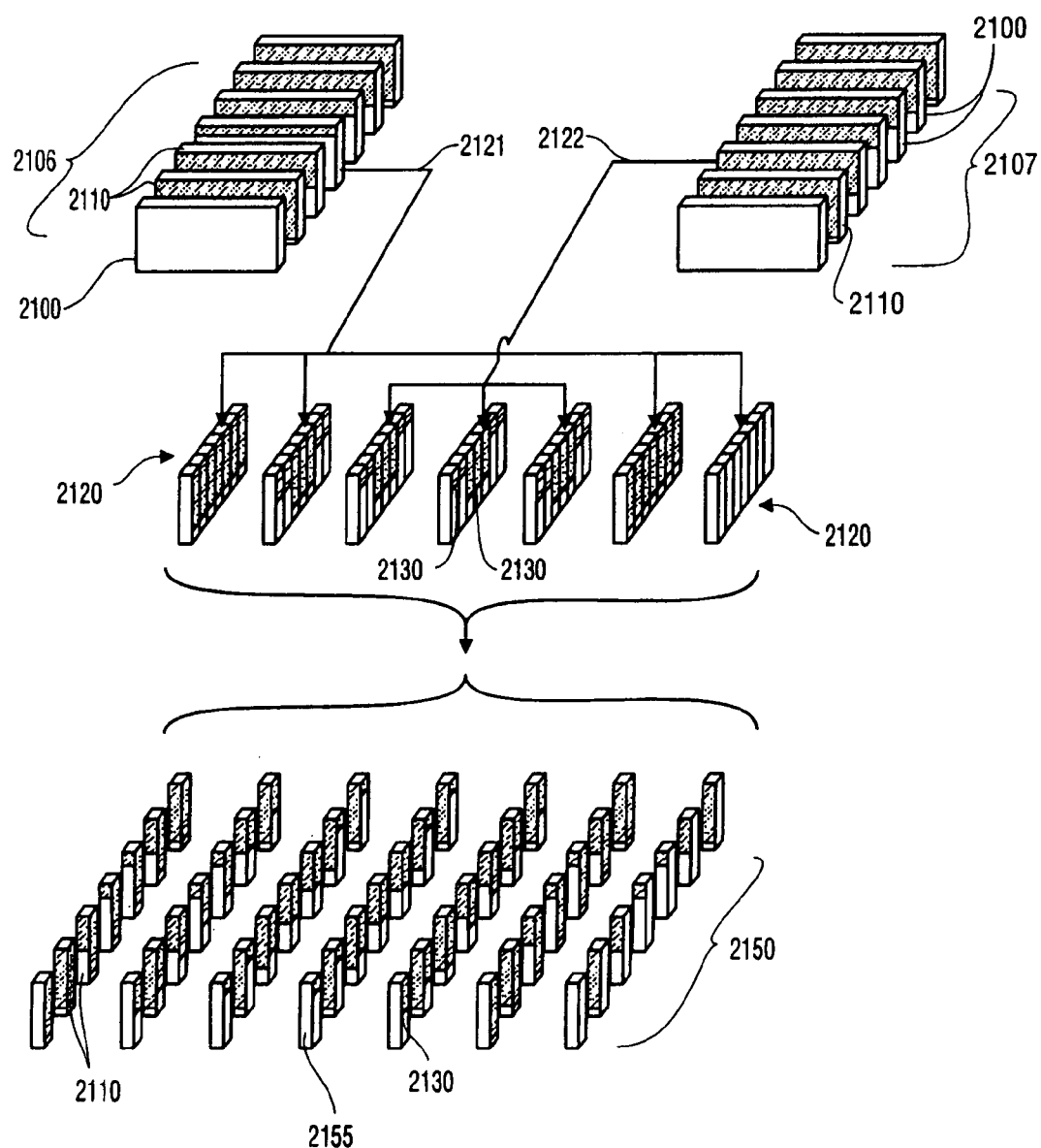
FIG. 28 illustrates an embodiment of the invention.

Table 1a and Table 1b show an example of the mask configuration of a 7×7 embodiment of a detector array made by the process of the invention. The information in Tables 1a and 1b are also illustrated in FIG. 28. Scintillation crystal slabs 2100, of a length longer than the intended detector array length, are painted with a number of linear masks 2110 of varying lengths. The crystal slabs are then glued together using an optical glue to form sandwich structures 2106, 2107.

The sandwiches 2106, 2107 are then cut into slices 2120. Slices from each sandwich type 2106, 2107 are chosen 2121, 2122 and a second set of masks 2130 are painted on the slices 2121, 2122. These slices 2121, 2122 are then glued together to form the final detector array 2150. The resulting detector array 2150, which when broken down into its component pieces, is comprised of individual crystals 2155 that have a first mask 2110 and a second mask 2130 painted on each of two of its facets 2155. When the masks 2110, 2130 on the crystals 2155 are viewed as a whole, the mask patterns are seen to be that of step functions that are coincident with each respective parallel plane formed by the crystals.

To illustrate the step functions on each of the parallel planes present in the detector array, Table 1a shows the mask depths of the first paint process, and Table 1b shows the mask depths of the second paint process.

TABLE 1a

| 7 × 7 First Paint (units = mm) | | | | | | | |
|---|---|---|---|---|---|---|---|
| | X1 | X2 | X3 | X4 | X5 | X6 | X7 |
| Y1 | 16.8 | 16.8 | 16.8 | 16.8 | 16.8 | 16.8 | 16.8 |
| Y2 | 8.4 | 8.4 | 13.3 | 13.3 | 13.3 | 8.4 | 8.4 |
| Y3 | 2.8 | 2.8 | 10.8 | 10.8 | 10.8 | 2.8 | 2.8 |
| Y4 | 2.8 | 2.8 | 10.8 | 10.8 | 10.8 | 2.8 | 2.8 |
| Y5 | 8.4 | 8.4 | 13.3 | 13.3 | 13.3 | 8.4 | 8.4 |
| Y6 | 16.8 | 16.8 | 16.8 | 16.8 | 16.8 | 16.8 | 16.8 |
| Y7 | 0 | 0 | 0 | 0 | 0 | 0 | 0 |

TABLE 1b

| 7 × 7 Second Paint (units = mm) | | | | | | |
|---|---|---|---|---|---|---|
| | X1 | X2 | X3 | X4 | X5 | X6 | X7 |
| Y1 | 16.8 | 8.4 | 2.8 | 2.8 | 8.4 | 16.8 | 0 |
| Y2 | 16.8 | 8.4 | 2.8 | 2.8 | 8.4 | 16.8 | 0 |
| Y3 | 16.8 | 13.3 | 10.8 | 10.8 | 13.3 | 16.8 | 0 |
| Y4 | 16.8 | 13.3 | 10.8 | 10.8 | 13.3 | 16.8 | 0 |
| Y5 | 16.8 | 13.3 | 10.8 | 10.8 | 13.3 | 16.8 | 0 |
| Y6 | 16.8 | 8.4 | 2.8 | 2.8 | 8.4 | 16.8 | 0 |
| Y7 | 16.8 | 8.4 | 2.8 | 2.8 | 8.4 | 16.8 | 0 |

Example 2

Table 2a and Table 2b show an example of the mask configuration of a 7×8 embodiment of a detector array made by the process of the invention. The information in Tables 2a and 2b are also illustrated in FIG. 29. Scintillation crystal slabs 2200, of a length longer than the intended detector array length, are painted with a number of linear masks 2210 of varying lengths. The crystal slabs are then glued together using an optical glue to form sandwich structures 2206, 2207, 2208, 2209.

The sandwiches 2206, 2207, 2208, 2209 are then cut into slices 2220. Slices from each sandwich type 2206, 2207, 2208, 2209 are chosen 2221, 2222, 2223, 2224 and a second set of masks 2230 are painted on the slices 2221, 2222, 2223, 2224. These slices 2221, 2222, 2223, 2224 are then glued together to form the final detector array 2250. The resulting detector array 2250, which when broken down into its component pieces, is comprised of individual crystals 2255 that have a first mask 2210 and a second mask 2230 painted on each of two of its facets 2255. When the masks 2210, 2230 on the crystals 2255 are viewed as a whole, the mask patterns are seen to be that of step functions that are coincident with each respective parallel plane formed by the crystals. In this example, the resulting detector array is an asymmetrical array. This array extends further over the PMTs 2260 in one direction than the usual symmetrical arrays.

To illustrate the step functions on each of the parallel planes present in the detector array, Table 2a shows the mask depths of the first paint process, and Table 2b shows the mask depths of the second paint process.

TABLE 2a

| 7 × 8 First Paint (units = mm) | | | | | | |
|---|---|---|---|---|---|---|
| | X1 | X2 | X3 | X4 | X5 | X6 | X7 |
| Y1 | 18 | 18 | 18 | 18 | 18 | 18 | 18 |
| Y2 | 12 | 12 | 12 | 13 | 12 | 12 | 12 |
| Y3 | 6 | 6 | 8 | 9 | 8 | 6 | 6 |
| Y4 | 0 | 2 | 5 | 7 | 5 | 2 | 0 |
| Y5 | 0 | 0 | 4 | 6 | 4 | 0 | 0 |
| Y6 | 2 | 2 | 7 | 7 | 7 | 2 | 2 |
| Y7 | 9 | 9 | 10 | 10 | 10 | 9 | 9 |
| Y8 | 0 | 0 | 0 | 0 | 0 | 0 | 0 |

TABLE 2b

| 7 × 8 Second Paint (units = mm) | | | | | | |
|---|---|---|---|---|---|---|
| | X1 | X2 | X3 | X4 | X5 | X6 | X7 |
| Y1 | 15 | 8 | 3 | 3 | 8 | 15 | 0 |
| Y2 | 17 | 10 | 5 | 5 | 10 | 17 | 0 |
| Y3 | 17 | 10 | 5 | 5 | 10 | 17 | 0 |
| Y4 | 17 | 10 | 5 | 5 | 10 | 17 | 0 |
| Y5 | 17 | 14 | 13 | 13 | 14 | 17 | 0 |
| Y6 | 17 | 14 | 13 | 13 | 14 | 17 | 0 |
| Y7 | 17 | 10 | 6 | 6 | 10 | 17 | 0 |
| Y8 | 17 | 10 | 6 | 6 | 10 | 17 | 0 |

Example 3

Figures 30A, 30B:
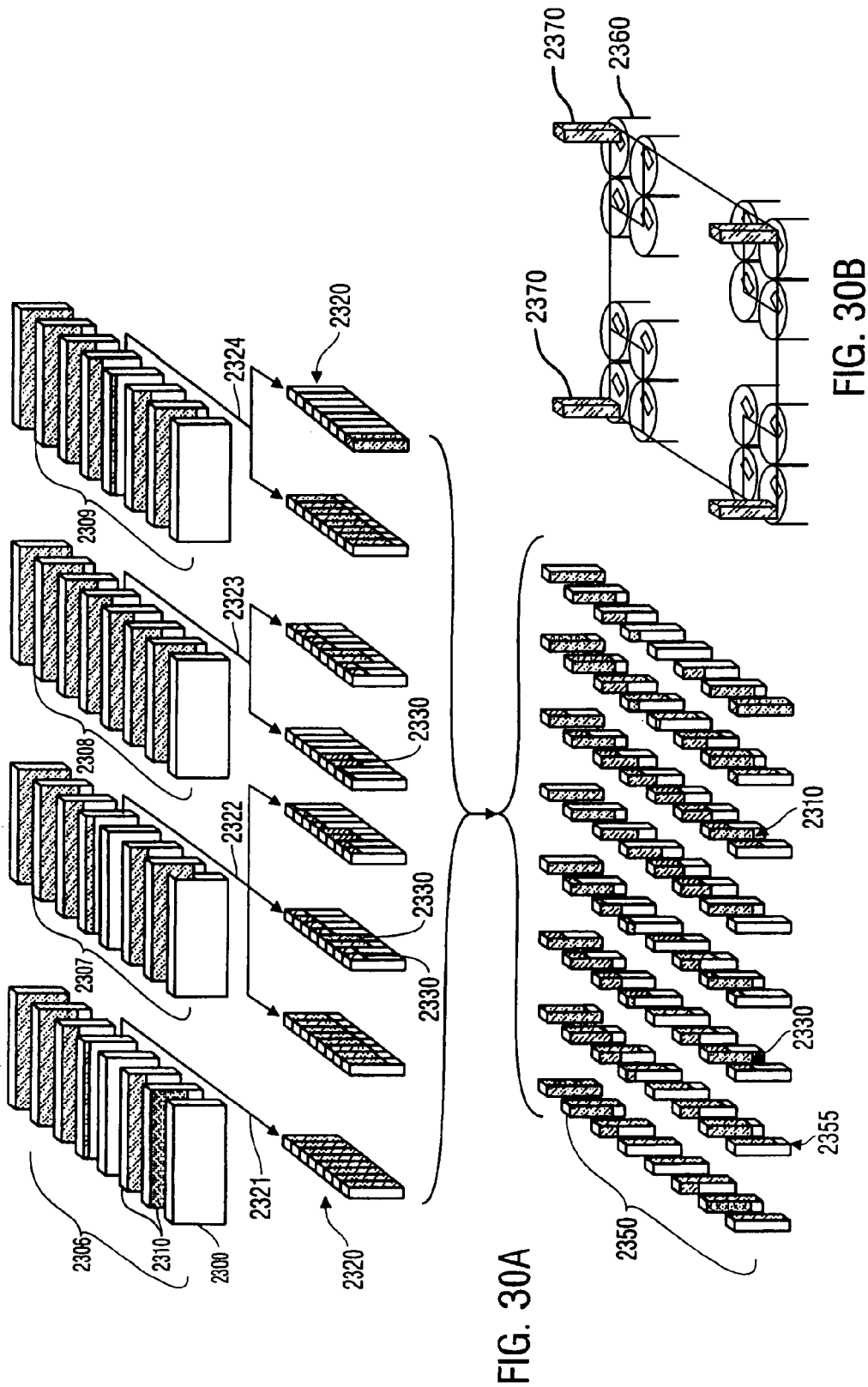
FIG. 30 illustrates another embodiment of the invention.

Table 3a and Table 3b show an example of the mask configuration of a 8×8 embodiment of a detector array made by the process of the invention. The information in Tables 3a and 3b are also illustrated in FIG. 30. Scintillation crystal slabs 2300, of a length longer than the intended detector array length, are painted with a number of linear masks 2310 of varying lengths. The crystal slabs are then glued together using an optical glue to form sandwich structures 2306, 2307, 2308, 2309.

The sandwiches 2306, 2307, 2308, 2309 are then cut into slices 2320. Slices from each sandwich type 2306, 2307, 2308, 2309 are chosen 2321, 2322, 2323, 2324 and a second set of masks 2330 are painted on the slices 2321, 2322, 2323, 2324. These slices 2321, 2322, 2323, 2324 are then glued together to form the final detector array 2350. The resulting detector array 2350, which when broken down into its component pieces, is comprised of individual crystals 2355 that have a first mask 2310 and a second mask 2330 painted on each of two of its facets 2355. When the masks 2310, 2330 on the crystals 2355 are viewed as a whole, the mask patterns are seen to be that of step functions that are coincident with each respective parallel plane formed by the crystals. In this example, the resulting detector array is an asymmetrical array.

This array extends further over the PMTs 2360 than the usual symmetrical arrays in 2 directions. One of its corner crystals 2370 is shaded as to indicate the relative orientation of the array (corner block) as the array would sit on each of the four corners of a module (similar to corner array 1920 shown in FIG. 26). Though not shown, the top 2nd, 3rd, and 4th slabs in the four sandwiches 2306, 2307, 2308, 2309, and the left 2nd, 3rd, and 4th slices 2322 are painted on both sides (double painted). The asymmetrical array will help in eliminating PMT waste in the in-plane circular dimension as it allows for coupling crystals to the PMTs in the area where no crystals had been coupled to the PMT using the traditional quadrant-sharing design.

To further extend the benefits of using asymmetrical scintillation arrays to aid in eliminating PMT waste, the asymmetrical arrays may be placed in a circular detector arrangement which will eliminate the PMT waste in the in-plane circular dimension. The process by which the asymmetrical array may be prepared for placement in a circular arrangement is the same as the process described earlier.

To illustrate the step functions on each of the parallel planes present in the detector array, Table 3a shows the mask depths of the first paint process, and Table 3b shows the mask depths of the second paint process, with the second mask of the double painted slabs and slices (not shown in FIG. 30).

TABLE 3a

8 × 8 First Paint (units = mm)

|    | X1        | X2        | X3        | X4        | X5        | X6        | X7        | X8        |
|----|-----------|-----------|-----------|-----------|-----------|-----------|-----------|-----------|
| Y1 | 18        | 18        | 18        | 18        | 18        | 18        | 18        | 18        |
| Y2 | 13.5 (18) | 14.5 (18) | 14.5 (18) | 14.5 (18) | 14.5 (18) | 14.5 (18) | 14.5 (18) | 14.5 (18) |
| Y3 | 6 (13.5)  | 7 (14.5)  | 7 (14.5)  | 7 (14.5)  | 11 (14.5) | 11 (14.5) | 7 (14.5)  | 7 (14.5)  |
| Y4 | 1 (6)     | 2 (7)     | 2 (7)     | 2 (7)     | 10 (11)   | 10 (11)   | 3 (7)     | 3 (7)     |
| Y5 | 0         | 0         | 0         | 0         | 9.5       | 9.5       | 1         | 1         |
| Y6 | 5.5       | 6.5       | 6.5       | 6.5       | 10.5      | 10.5      | 6.5       | 6.5       |
| Y7 | 14        | 15        | 15        | 15        | 15        | 15        | 15        | 15        |
| Y8 | 0         | 0         | 0         | 0         | 0         | 0         | 0         | 0         |

TABLE 3b

8 × 8 Second Paint (units = mm)

|    | X1 | X2        | X3        | X4       | X5  | X6   | X7 | X8 |
|----|----|-----------|-----------|----------|-----|------|----|----|
| Y1 | 18 | 13.5 (18) | 6 (13.5)  | 1 (6)    | 0   | 5.5  | 14 | 0  |
| Y2 | 18 | 14.5 (18) | 7 (14.5)  | 2 (7)    | 0   | 6.5  | 15 | 0  |
| Y3 | 18 | 14.5 (18) | 7 (14.5)  | 2 (7)    | 0   | 6.5  | 15 | 0  |
| Y4 | 18 | 14.5 (18) | 7 (14.5)  | 2 (7)    | 0   | 6.5  | 15 | 0  |
| Y5 | 18 | 14.5 (18) | 11 (14.5) | 10 (11)  | 9.5 | 10.5 | 15 | 0  |
| Y6 | 18 | 14.5 (18) | 11 (14.5) | 10 (11)  | 9.5 | 10.5 | 15 | 0  |
| Y7 | 18 | 14.5 (18) | 7 (14.5)  | 3 (7)    | 1   | 6.5  | 15 | 0  |
| Y8 | 18 | 14.5 (18) | 7 (14.5)  | 3 (7)    | 1   | 6.5  | 15 | 18 |

REFERENCES

These references are herein incorporated by reference in their entirety.

[1] J Uribe, H. Baghaei, H. Li, et al, "Basic imaging performance characteristics of a variable field of view PET using quadrant sharing detectors," IEEE Trans. Nucl. Sci., vol 46, no. 6, pp. 491–497, 1999
[2] W-H. Wong, "A positron camera detector design with cross coupled scintillators and quadrant sharing photomultipliers," IEEE Trans. Nucl. Sci., vol 40, pp. 962–966, 1993
[3] M. P. Tomai, G. Germano, E. J. Hoffman, "Position and energy response of PET block detectors with different light sharing schemes," IEEE Trans. Nucl. Sci., vol 41 (4), pp. 1458–1463, 1994
[4] W-H. Wong, S. Yokoyama, J. Uribe, et al, "An elongated position sensitive block detector design using the PMT quadrant sharing detector array," IEEE Trans. Nucl. Sci., vol 46(3), pp. 542–545, 1999
[5] M. Aykac, J. Uribe, H. Baghaei, H. Li, Y. Wang, Y. Liu, Tao Xing and W. H. Wong, "Septa Design Study for Volumetric Imaging in Positron Emission Tomography", IEEE MIC Conference Record 2001.
[6] H. Li, W-H Wong, J. Uribe, et al, "A high speed position-decoding electronics for BGO block detectors in PET," IEEE Trans. Nucl. Sci., vol 47 (3), pp. 1006–1010, 2000
[7] W-H Wong, H. Li, J. Uribe, et al, "Feasibility of a high speed gamma camera using the high-yield-pileup-event-recovery (HYPER) method," J. Nucl. Med., 42 (4), pp624–632, 2001.
[8] H. Li, W-H Wong, J. Uribe, et al, "A new pileup prevention front-end electronic design for high resolution PET and gamma cameras," IEEE MIC Conference Record 2001.
[9] W-H Wong, J. Uribe, H. Li, H. Baghaei, Y. Wang, M. Aykac, Y. Liu, T. Xing, and D. Bilgen, "The Design of A High Resolution Transformable Wholebody PET Camera," IEEE Medical Imaging Conference, Nov. 10, 2001.
[10] J. Uribe, M. Aykac, H. Baghaei, H. Li, Y. Wang, Y. Liu, T. Xing and Wai-Hoi Wong, "Inexpensive Position Sensitive Detector Block for 40 mm Diameter PMT Using Quadrant Sharing Configuration," IEEE Medical Imaging Conference, Nov. 10, 2001.

What is claimed is:

1. An apparatus, comprising:
a plurality of photomultiplier tubes; and
a scintillation crystal array coupled to the plurality of photomultiplier tubes, the scintillation crystal array defining a plurality of corners;
wherein a first corner of the plurality of corners is aligned with a first center of a first photomultiplier tube of the plurality of photomultiplier tubes and a second corner of the plurality of corners is not aligned with a second center of a second photomultiplier tube of the plurality of photomultiplier tubes;
wherein the scintillation crystal array comprises a pentagonal block of crystals; and
wherein the pentagonal block is tapered in accordance with the following equation:

$$T = W/\cos^2(180°/N) - 2D \tan(180°/N)$$

where T is a taper amount, W is a width of the scintillation crystal array, D is a depth of the scintillation crystal array, and N is a number.

2. The apparatus of claim 1, wherein a third corner of the plurality of corners is not aligned with a third center of a third of the plurality of photomultiplier tubes.

3. The apparatus of claim 1, wherein the scintillation crystal array includes n×m crystals selected from the group consisting of bismuth germanium oxide, germanium silicate, and lutetium oxyorthosilicate, where n is a width of the scintillation crystal array and m is a length of the scintillation crystal array.

4. The apparatus of claim 2, wherein a fourth corner of the plurality of corners is not aligned with a fourth center of a fourth of the photomultiplier tubes.

5. The apparatus of claim 4, wherein the scintillation crystal array includes $n^2$ crystals selected from the group consisting of bismuth germanium oxide, germanium silicate, and lutetium oxyorthosilicate, where n is a matrix size of the scintillation crystal array.

6. The apparatus of claim 1, further comprising another scintillation crystal array coupled to the first photomultiplier tube of the plurality of photomultiplier tubes, the another scintillation crystal array defining another corner that is aligned with the first center of the first of the plurality of photomultiplier tubes.

7. The apparatus of claim 1, further comprising a light guide coupled between the plurality of photomultiplier tubes and the scintillation crystal array.

8. The apparatus of claim 1, wherein the pentagonal block of the scintillation crystal array is tapered in an in-plane dimension of the scintillation crystal array.

9. A positron emission tomography camera comprising the apparatus of claim 1.

10. The apparatus of claim 1, the plurality of photomultiplier tubes configured in a circular system.

11. A method, comprising:
coupling a plurality of photomultiplier tubes to a scintillation crystal array, the scintillation crystal array defining a plurality of corners,
wherein a first corner of the plurality of corners is aligned with a first center of a first photomultiplier tube of the plurality of photomultiplier tubes and a second corner of the plurality of corners is not aligned with a second center of a second photomultiplier tube of the plurality of photomultiplier tubes;
wherein the scintillation crystal array comprises a pentagonal block of crystals; and
wherein the pentagonal block is tapered in accordance with the following equation:

$$T = W/\cos^2(180°/N) - 2D \tan(180°/N)$$

where T is a taper amount, W is a width of the scintillation crystal array, D is a depth of the scintillation crystal array, and N is a number.

12. The method of claim 11, wherein a third corner of the plurality of corners is not aligned with a third center of a third of the plurality of photomultiplier tubes.

13. The method of claim 12, wherein a fourth corner of the plurality of corners is not aligned with a fourth center of a fourth of the photomultiplier tubes.

14. The method of claim 13, wherein the scintillation crystal array includes $n^2$ crystals selected from the group consisting of bismuth germanium oxide, germanium silicate, and lutetium oxyorthosilicate.

15. The method of claim 11, wherein the scintillation crystal array includes n×m crystals selected from the group consisting of bismuth germanium oxide, germanium silicate, and lutetium oxyorthosilicate.

16. The method of claim 11, further comprising coupling another scintillation crystal array to the first photomultiplier tube of the plurality of photomultiplier tubes, the another scintillation crystal array defining another corner that is aligned with the first center of the first of the plurality of photomultiplier tubes.

17. The method of claim 11, further comprising coupling a light guide between the plurality of photomultiplier tubes and the scintillation crystal array.

18. The method of claim 11, wherein the pentagonal block of the scintillation crystal array is tapered in an in-plane dimension of the scintillation crystal array.

19. A method, comprising detecting radiation with a scintillation crystal array coupled to a plurality of photomultiplier tubes, the scintillation crystal array defining a plurality of corners;

wherein a first corner of the plurality of corners is aligned with a first center of a first photomultiplier tube of the plurality of photomultiplier tubes and a second corner of the plurality of corners is not aligned with a second center of a second photomultiplier tube of the plurality of photomultiplier tubes;
wherein the scintillation crystal array comprises a pentagonal block of crystals; and
wherein the pentagonal block is tapered in accordance with the following equation:

$$T = W/\cos^2(180°/N) - 2D \tan(180°/N)$$

where T is a taper amount, W is a width of the scintillation crystal array, D is a deDth of the scintillation crystal array, and N is a number.

20. The method of claim 19, wherein a third corner of the plurality of corners is not aligned with a third center of a third of the plurality of photomultiplier tubes.

21. The method of claim 20, wherein a fourth corner of the plurality of corners is not aligned with a fourth center of a fourth of the photomultiplier tubes.

22. The method of claim 21, wherein the scintillation crystal array includes $n^2$ crystals selected from the group consisting of bismuth germanium oxide and lutetium oxyorthosilicate.

23. The method of claim 19, wherein the scintillation crystal array includes n×m crystals selected from the group consisting of bismuth germanium oxide, germanium silicate, and lutetium oxyorthosilicate.

24. The method of claim 19, further comprising coupling another scintillation crystal array to the first photomultiplier tube of the plurality of photomultiplier tubes, the another scintillation crystal array defining another corner that is aligned with the first center of the first of the plurality of photomultiplier tubes.

25. The method of claim 19, further comprising guiding a photon from the scintillation crystal array to at least one of the plurality of photomultiplier tubes via a light guide.

26. An apparatus, comprising:
a plurality of photomultiplier tubes configured as a continuous detector-ring; and
a scintillation crystal array coupled to the plurality of photomultiplier tubes, the scintillation crystal array comprising a plurality of pentagonal blocks of crystals tapered in accordance with the following equation:

$$T = W/\cos^2(180°/N) \times 2D \tan(180°/N)$$

where T is a taper amount, W is a width of the scintillation crystal array, D is a depth of the scintillation crystal array, and N is a number.

27. The apparatus of claim 26, the plurality of pentagonal blocks of crystals comprising equal-entrance-width crystals.

28. The apparatus of claim 26, the plurality of pentagonal blocks of crystals comprising equal-production-slice thickness crystals.

29. The apparatus of claim 26, the continuous detector-ring comprising a circular system.

* * * * *

UNITED STATES PATENT AND TRADEMARK OFFICE
CERTIFICATE OF CORRECTION

| | | |
|---|---|---|
| PATENT NO. | : 7,238,943 B2 | Page 1 of 1 |
| APPLICATION NO. | : 10/356679 | |
| DATED | : July 3, 2007 | |
| INVENTOR(S) | : Wong et al. | |

It is certified that error appears in the above-identified patent and that said Letters Patent is hereby corrected as shown below:

In claim 19, column 24, line 15, delete "deDth" and insert --depth-- therefor.

Signed and Sealed this

Fourth Day of September, 2007

JON W. DUDAS
*Director of the United States Patent and Trademark Office*

UNITED STATES PATENT AND TRADEMARK OFFICE
CERTIFICATE OF CORRECTION

PATENT NO.       : 7,238,943 B2                                          Page 1 of 1
APPLICATION NO.  : 10/356679
DATED            : July 3, 2007
INVENTOR(S)      : Wai-Hoi Wong et al.

It is certified that error appears in the above-identified patent and that said Letters Patent is hereby corrected as shown below:

In the specification:

Column 1, lines 17-19, delete the entire paragraph and insert the following paragraph therefor:

--This invention was made with government support from the National Institutes of Health (NIH RO1 CA 61880; NIH RO1 CA 58980). The Government has certain rights in the invention.--

Signed and Sealed this

Sixteenth Day of October, 2007

JON W. DUDAS
*Director of the United States Patent and Trademark Office*